United States Patent
Moein et al.

(10) Patent No.: US 9,271,670 B2
(45) Date of Patent: *Mar. 1, 2016

(54) CONNECTORS FOR MAKING CONNECTIONS BETWEEN ANALYTE SENSORS AND OTHER DEVICES

(71) Applicant: Abbott Diabetes Care Inc., Alameda, CA (US)

(72) Inventors: Mohammad E. Moein, Saratoga, CA (US); Louis G. Pace, San Carlos, CA (US); Udo Hoss, Castro Valley, CA (US); Phu X. Le, Dublin, CA (US); Samuel M. Curry, San Francisco, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/685,304

(22) Filed: Apr. 13, 2015

(65) Prior Publication Data

US 2015/0216455 A1    Aug. 6, 2015

Related U.S. Application Data

(63) Continuation of application No. 13/526,136, filed on Jun. 18, 2012, now Pat. No. 9,007,781.

(60) Provisional application No. 61/498,142, filed on Jun. 17, 2011.

(51) Int. Cl.
*H05K 5/00* (2006.01)
*A61B 5/1473* (2006.01)
(Continued)

(52) U.S. Cl.
CPC .............. *A61B 5/1473* (2013.01); *A61B 5/1468* (2013.01); *A61B 5/1486* (2013.01); *A61B 5/14532* (2013.01); *A61B 5/14546* (2013.01); *A61B 5/4839* (2013.01); *A61B 5/6848* (2013.01); *H05K 3/325* (2013.01);
(Continued)

(58) Field of Classification Search
USPC ................. 361/728–730, 748, 759, 760, 721; 174/260–262
See application file for complete search history.

(56) References Cited

U.S. PATENT DOCUMENTS

| | | |
|---|---|---|
| 4,572,604 A | 2/1986 | Ammon et al. |
| 5,262,035 A | 11/1993 | Gregg et al. |

(Continued)

FOREIGN PATENT DOCUMENTS

| | | |
|---|---|---|
| GB | 1323873 | 7/1973 |
| WO | WO 2006/087984 | 8/2006 |

(Continued)

*Primary Examiner* — Hung S Bui
(74) *Attorney, Agent, or Firm* — Edward J. Baba; Brian E. Davy; Bozicevic, Field & Francis LLP

(57) ABSTRACT

Analyte sensor connectors that connect analyte sensors, e.g., conductive members of analyte sensors, to other devices such as sensor electronics units, e.g., sensor control units, are provided. Also provided are systems that include analyte sensors, analyte sensor connectors, and analyte sensor electronics units, as well as methods of establishing and maintaining connections between analyte sensors and analyte sensor electronics units, and methods of analyte monitoring/detection. Also provided are methods of making analyte sensor connectors and systems that include analyte sensor connectors.

23 Claims, 27 Drawing Sheets

(51) Int. Cl.
*A61B 5/00* (2006.01)
*A61B 5/145* (2006.01)
*A61B 5/1468* (2006.01)
*A61B 5/1486* (2006.01)
*H05K 3/32* (2006.01)
*H01L 23/00* (2006.01)
*H05K 3/36* (2006.01)

(52) U.S. Cl.
CPC ............ *A61B2562/227* (2013.01); *H01L 24/72* (2013.01); *H01L 2924/07811* (2013.01); *H01L 2924/12042* (2013.01); *H05K 3/365* (2013.01); *H05K 2201/053* (2013.01); *H05K 2201/10151* (2013.01); *H05K 2201/10401* (2013.01); *H05K 2201/10409* (2013.01); *Y10T 29/4913* (2015.01)

(56) References Cited

U.S. PATENT DOCUMENTS

| | | |
|---|---|---|
| 5,262,305 A | 11/1993 | Heller et al. |
| 5,264,104 A | 11/1993 | Gregg et al. |
| 5,311,057 A | 5/1994 | McShane |
| 5,320,715 A | 6/1994 | Berg |
| 5,381,047 A | 1/1995 | Kanno |
| 5,520,787 A | 5/1996 | Hanagan et al. |
| 5,593,852 A | 1/1997 | Heller et al. |
| 5,600,183 A | 2/1997 | Gates, Jr. et al. |
| 5,916,425 A | 6/1999 | Leader et al. |
| 6,117,290 A | 9/2000 | Say et al. |
| 6,175,752 B1 | 1/2001 | Say et al. |
| 6,650,471 B2 | 11/2003 | Doi |
| 6,736,957 B1 | 5/2004 | Forrow et al. |
| 6,746,582 B2 | 6/2004 | Heller et al. |
| 7,501,053 B2 | 3/2009 | Karinka et al. |
| 7,754,093 B2 | 7/2010 | Forrow et al. |
| 7,811,231 B2 | 10/2010 | Jin et al. |
| 7,869,218 B2 | 1/2011 | Ni et al. |
| 7,879,211 B2 | 2/2011 | Katsuki et al. |
| 8,278,948 B2 | 10/2012 | Johnson |
| 8,377,273 B2 | 2/2013 | Yasuda et al. |
| 2008/0135408 A1 | 6/2008 | Sjolander |
| 2009/0060789 A1 | 3/2009 | Aas et al. |
| 2010/0063374 A1 | 3/2010 | Goodnow et al. |
| 2010/0081905 A1 | 4/2010 | Bommakanti et al. |
| 2010/0230285 A1 | 9/2010 | Hoss et al. |
| 2011/0021889 A1 | 1/2011 | Hoss et al. |
| 2011/0077490 A1 | 3/2011 | Simpson et al. |
| 2011/0288574 A1 | 11/2011 | Curry et al. |
| 2011/0319729 A1 | 12/2011 | Donnay et al. |
| 2012/0010642 A1 | 1/2012 | Lee et al. |

FOREIGN PATENT DOCUMENTS

| | | |
|---|---|---|
| WO | WO 2008/143943 | 11/2008 |
| WO | WO 2010/009463 | 1/2010 |
| WO | WO 2011/025549 | 3/2011 |

LAYER 1 BOTTOM - WORKING ELECTRODE TRACE

LAYER 2 BOTTOM - DIELECTRIC

LAYER 3 BOTTOM - REFERENCE ELECTRODE TRACE

LAYER 4 BOTTOM - DIELECTRIC

FIG. 13 LAYER 5 TOP COUNTER ELECTRODE TRACE

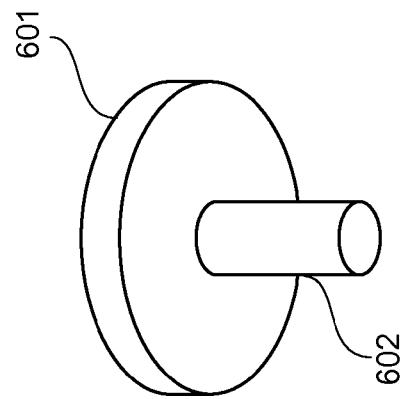
FIG. 15B
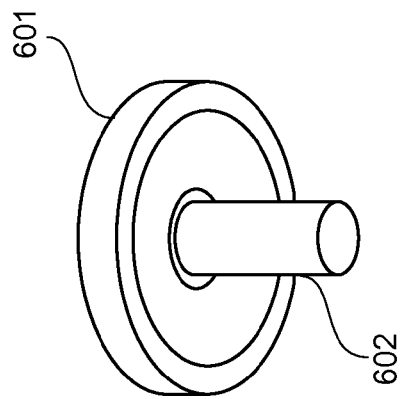
FIG. 15E
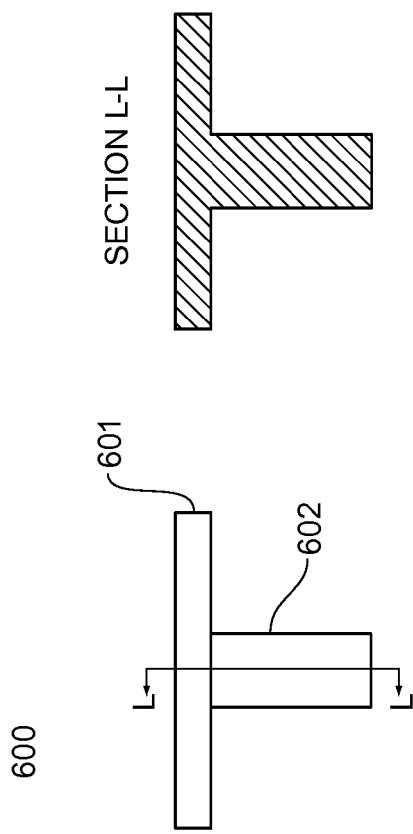
FIG. 15A
FIG. 15C
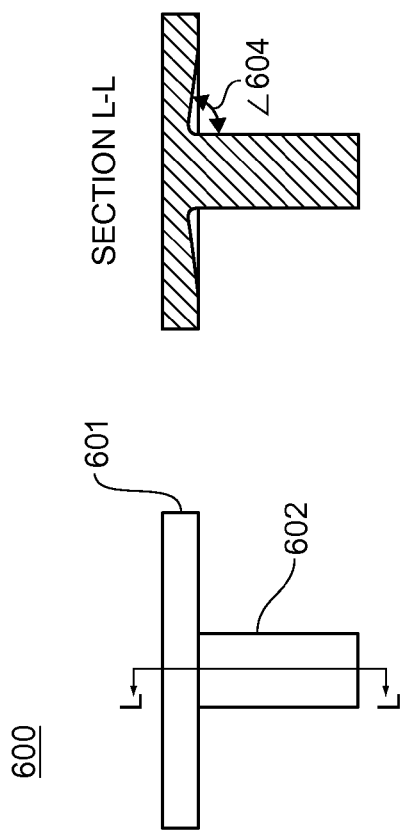
FIG. 15D
FIG. 15F

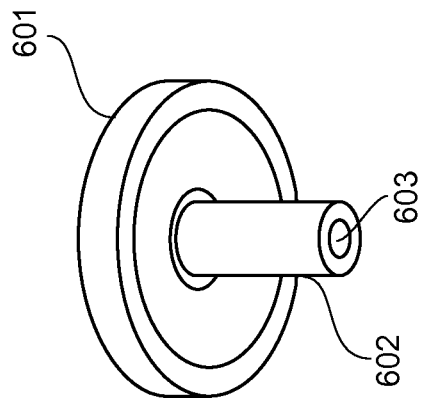
FIG. 15G / FIG. 15H / FIG. 15I
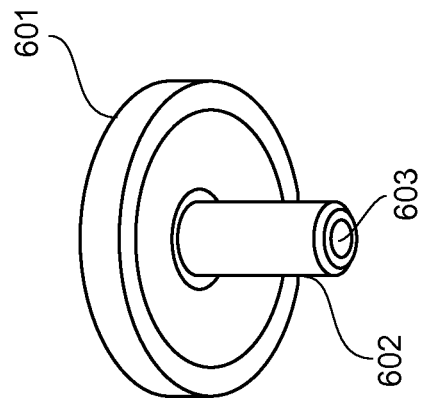
FIG. 15J / FIG. 15K / FIG. 15L

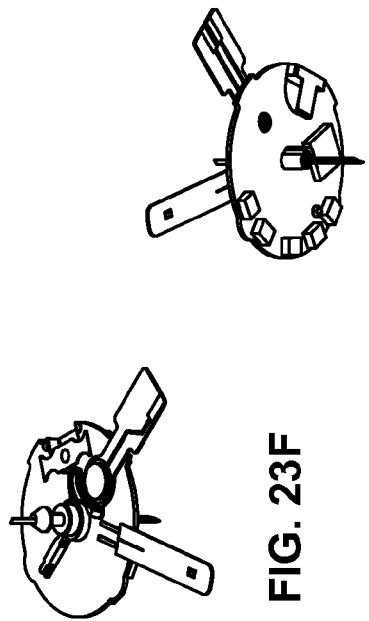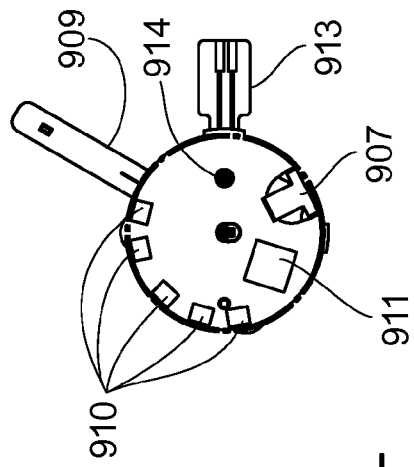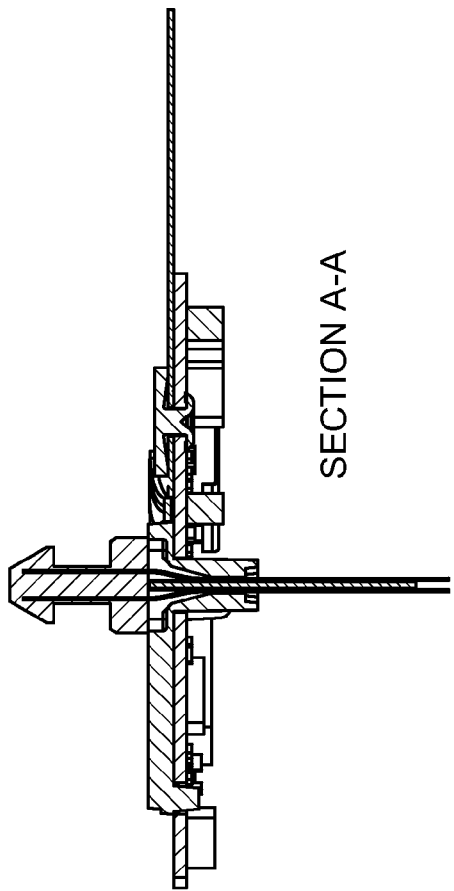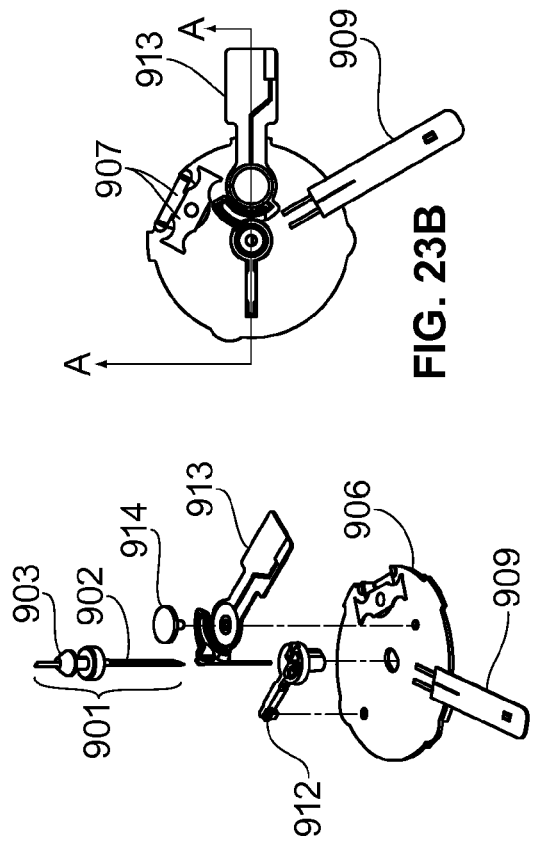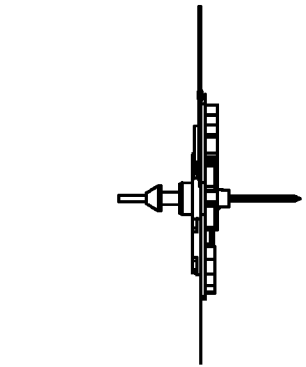

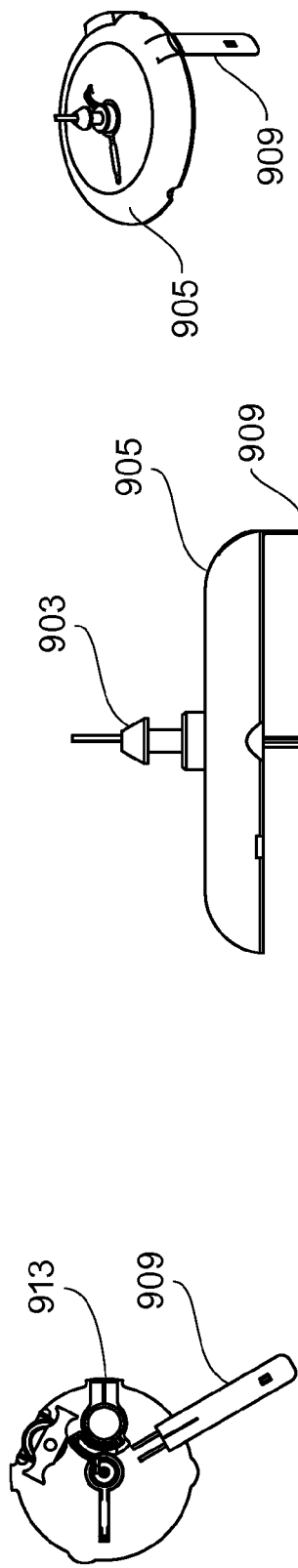
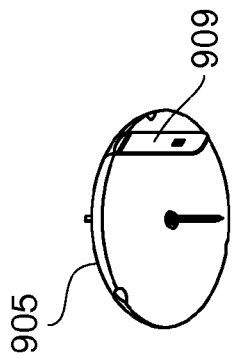
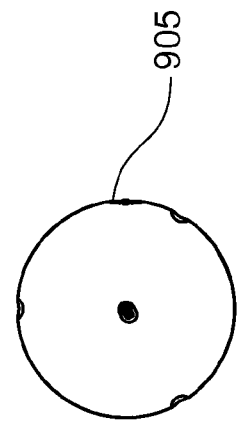
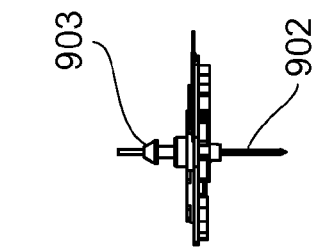
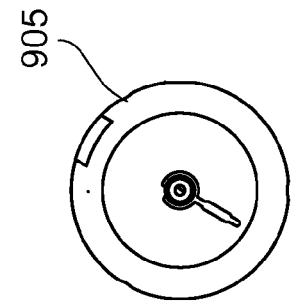
FIG. 24A  FIG. 24B  FIG. 24C  FIG. 24D  FIG. 24E  FIG. 24F  FIG. 24G

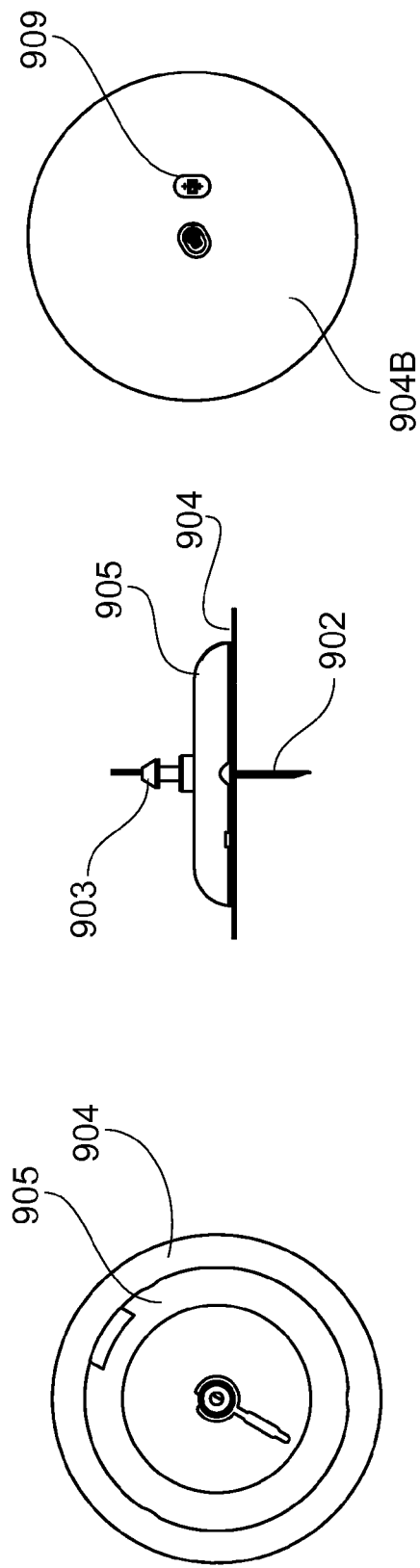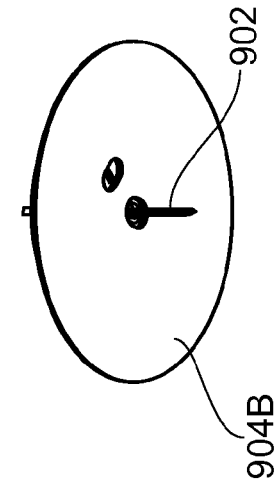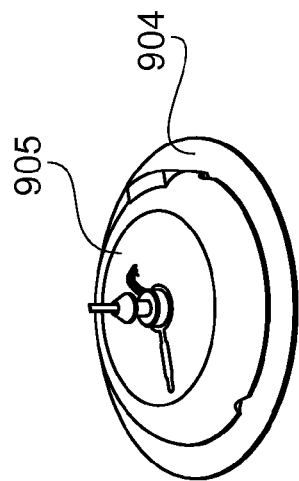

ND OTHER DEVICES

CONNECTORS FOR MAKING CONNECTIONS BETWEEN ANALYTE SENSORS AND OTHER DEVICES

CROSS-REFERENCE TO RELATED APPLICATIONS

This application is a continuation of U.S. application Ser. No. 13/526,136, filed on Jun. 18, 2012, which application claims priority based on U.S. Provisional Application No. 61/498,142, filed Jun. 17, 2011, the disclosure of which is incorporated by reference herein.

INTRODUCTION

In many instances it is desirable or necessary to regularly monitor the concentration of particular constituents in a fluid. A number of systems are available that analyze the constituents of bodily fluids such as blood, urine and saliva. Examples of such systems may be configured to monitor the level of particular medically significant fluid constituents, such as, for example, cholesterol, ketones, vitamins, proteins, and various metabolites or blood sugars, such as glucose. Diagnosis and management of patients suffering from diabetes mellitus, a disorder of the pancreas where insufficient production of insulin prevents normal regulation of blood sugar levels, generally requires careful monitoring of blood glucose levels on a daily basis.

A number of systems that allow individuals to easily monitor their blood glucose are currently available. For example, a person may obtain a blood sample by withdrawing blood from a blood source in his or her body, such as a vein, using a needle and syringe, for example, or by lancing a portion of his or her skin, using a lancing device, for example, to make blood available external to the skin, to obtain the necessary sample volume for in vitro testing. The person may then apply the blood sample to a test strip, whereupon suitable detection methods, such as calorimetric, electrochemical, or photometric detection methods, for example, may be used to determine the person's actual blood glucose level. The foregoing procedure provides a blood glucose concentration for a particular or discrete point in time, and thus, must be repeated periodically when the user actively initiates the procedure, in order to monitor blood glucose over a longer period.

In addition to the discrete or periodic, in vitro, blood glucose-monitoring systems described above, there are at least partially implantable, or in vivo, blood glucose-monitoring systems, which are constructed to provide continuous or automatic in vivo measurement of an individual's blood glucose concentration. Such in vivo analyte monitoring devices are constructed to provide for continuous or automatic monitoring of analytes, such as glucose, in the blood stream or interstitial fluid while the in vivo analyte monitoring device is positioned at least partially in the body of a user. Such devices include analyte sensors, e.g., electrochemical sensors, at least a portion of which are operably positioned in a blood vessel or in the subcutaneous tissue of a user, or elsewhere, for monitoring/detection.

While continuous or automatic glucose monitoring is desirable, there are several challenges associated with manufacturing sensors constructed for in vivo use. In addition, attaching such sensors to other system components such as electronics units, e.g., sensor control units, poses additional challenges, particularly where two or more electrodes and their respective conductive traces are positioned on different surfaces of the sensor, e.g., on opposing substrate surfaces. Accordingly, further development of manufacturing techniques and methods; as well as analyte monitoring devices, systems, and kits employing the same, are desirable and provided herein.

SUMMARY

Analyte sensor connectors that connect analyte sensors, e.g., conductive members of analyte sensors, to other devices such as sensor electronics units, e.g., sensor control units, are provided. Also provided are systems that include analyte sensors, analyte sensor connectors, and analyte sensor electronics units, as well as methods of establishing and maintaining connections between analyte sensors and analyte sensor electronics units, and methods of analyte monitoring/detection. Also provided are methods of making analyte sensor connectors and systems that include analyte sensor connectors.

Embodiments of the present disclosure relate to analyte monitoring and/or detection devices and systems which utilize one or more sensor connectors, e.g., one or more rivets, to physically connect an analyte sensor, e.g., an in vivo or in vitro analyte sensor having one or more electrodes to an electronics unit such as a sensor control unit. Also provided, are systems and devices which utilize one or more conductive sensor connectors, e.g., conductive rivets, to electrically connect an analyte sensor, e.g., an in vivo or in vitro analyte sensor, having one or more electrodes to an electronics unit such as a sensor control unit, e.g., by electrically connecting one or more electrodes disposed on a first surface of the analyte sensor with one or more electrical contacts disposed on a second surface of the analyte sensor or a surface of the electronics unit.

Methods of making and using the analyte monitoring systems and devices, as well as methods of analyte monitoring and kits are provided. Also provided are analyte sensors and analyte sensor precursors along with methods of making and using the same.

BRIEF DESCRIPTION OF THE DRAWINGS

A detailed description of various embodiments of the present disclosure is provided herein with reference to the accompanying drawings, which are briefly described below. The drawings are illustrative and are not necessarily drawn to scale. The drawings illustrate various embodiments of the present disclosure and may illustrate one or more embodiment(s) or example(s) of the present disclosure in whole or in part. A reference numeral, letter, and/or symbol that is used in one drawing to refer to a particular element may be used in another drawing to refer to a like element.

FIG. 15A shows a side view of one embodiment of a rivet which may be used in connection with the present disclosure.

FIG. 15B shows a cross-section taken along section L-L of FIG. 15A.

FIG. 15C shows a bottom perspective view of the rivet depicted in FIG. 15A.

FIG. 15D shows a side view of one embodiment of a rivet which may be used in connection with the present disclosure.

FIG. 15E shows a cross-section taken along section L-L of FIG. 15D.

FIG. 15F shows a bottom perspective view of the rivet depicted in FIG. 15D.

FIG. 15G shows a side view of one embodiment of a rivet which may be used in connection with the present disclosure.

FIG. 15H shows a cross-section taken along section L-L of FIG. 15G.

FIG. 15I shows a bottom perspective view of the rivet depicted in FIG. 15G.

FIG. 15J shows a side view of one embodiment of a rivet which may be used in connection with the present disclosure.

FIG. 15K shows a cross-section taken along section L-L of FIG. 15J.

FIG. 15L shows a bottom perspective view of the rivet depicted in FIG. 15J.

FIGS. 23A-23G provide an exploded view (23A), top view (23B), side view (23C), bottom view (23D), cross-section (23E) taken along section A-A of (23B), a top perspective view (23F) and a bottom perspective view (23G), of a portion of the sensor control unit insertion assembly depicted in FIGS. 21A and 21B including a PCB assembly, sensor support, analyte sensor, rivet and sensor insertion device. The analyte sensor is shown prior to cutting, e.g., along the cut line shown in FIG. 7, to remove excess sensor material.

FIGS. 24A-24G provide a top view (24A) and a side view (24B) of the portion of the sensor control unit insertion assembly depicted in FIGS. 24A-24G. Here, the analyte sensor is shown after cutting, e.g., along the cut line shown in FIG. 7, to remove excess sensor material. Also provided, is a top view (24C), a side view (24D), a bottom view (24E), a top perspective view (24F) and a bottom perspective view (24G) of a portion of the sensor control unit insertion assembly depicted in FIGS. 21A and 21B including the PCB assembly, sensor support, analyte sensor, rivet, sensor insertion device and overmold structure. An optional thermistor of the PCB assembly is shown in a partially folded configuration.

FIGS. 26A-26E provide a top view (26A), a side view (26B), a bottom view (26C), a top perspective view (26D) and a bottom perspective view (26E) of the sensor control unit insertion assembly depicted in FIGS. 21A and 21B, including the overmold structure and the skin patch.

DETAILED DESCRIPTION

Figure 1A:
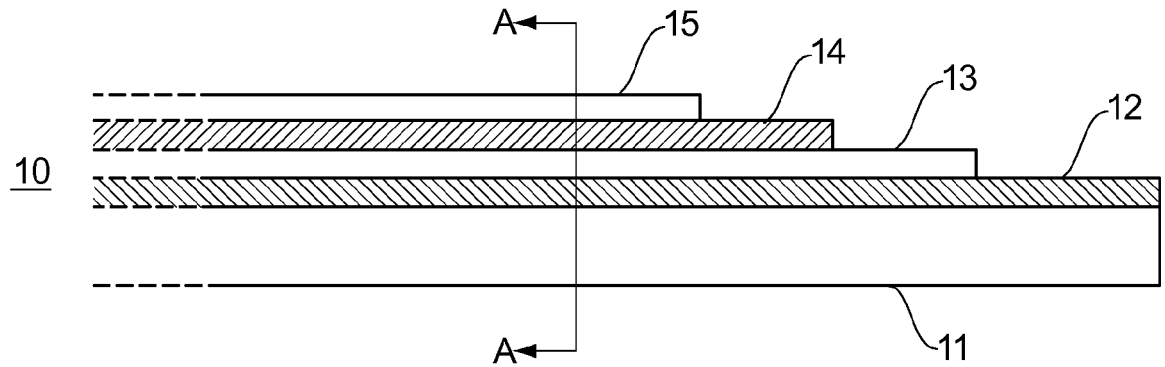
FIG. 1A shows a cross-sectional view of a distal portion of an analyte sensor according to the present disclosure.

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting, since the scope of the embodiments of the invention will be embodied by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

In the description of the invention herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

It is further noted that the claims may be drafted to exclude any recited element. As such, this statement is intended to serve as antecedent basis for use of such exclusive terminology as "solely," "only" and the like in connection with the recitation of claim elements, or use of a "negative" limitation.

Various terms are described below to facilitate an understanding of the invention. It will be understood that a corresponding description of these various terms applies to corresponding linguistic or grammatical variations or forms of these various terms. It will also be understood that the invention is not limited to the terminology used herein, or the descriptions thereof, for the description of particular embodiments. Merely by way of example, the invention is not limited to particular analytes, bodily or tissue fluids, blood or capillary blood, or sensor constructs or usages, unless implicitly or explicitly understood or stated otherwise, as such may vary.

To the extent any definition of a term defined herein conflicts with a definition of a term in an application or reference incorporated by reference herein, the instant application shall control.

The publications discussed herein are provided solely for their disclosure prior to the filing date of the application. Nothing herein is to be construed as an admission that the embodiments of the invention are not entitled to antedate such publication by virtue of prior invention. Further, the dates of publication provided may be different from the actual publication dates which may need to be independently confirmed.

Generally, embodiments of the present disclosure relate to methods, devices systems, and related kits for detecting and/or monitoring at least one analyte, such as glucose, in body fluid. Embodiments relate to the continuous and/or automatic in vivo detection and/or monitoring of the level of one or more analytes using a continuous analyte monitoring system that includes an analyte sensor for the in vivo detection and/or monitoring of at least one analyte, such as glucose, lactate, oxygen, ketones, and the like, in a body fluid. Embodiments include wholly implantable analyte sensors and transcutaneous analyte sensors in which only a portion of the sensor is positioned under the skin and a portion of the sensor resides above the skin, e.g., for contact to an electronics unit (e.g., a sensor control unit), a communication device, (e.g., a transmitter, receiver, transceiver, radio frequency identification (RFID) tag or reader), a processor, etc. Additional information regarding RFID tags and readers is provided, for example, in U.S. Patent Application Publication No. 2010/0063374, the disclosure of which is incorporated by reference herein.

At least a portion of a sensor may be, for example, subcutaneously positionable in a patient for the continuous or semi-continuous monitoring of a level of an analyte in a patient's interstitial fluid. For the purposes of this description, the term continuous monitoring encompasses semi-continuous monitoring unless noted otherwise. The sensor response, for example if obtained from non-blood samples, may be correlated and/or converted to analyte levels in blood or other fluids. In certain embodiments, an analyte sensor may be positioned in contact with interstitial fluid to detect the level of glucose, which detected glucose may be used to infer the glucose level in the patient's bloodstream. Analyte sensors may be insertable into a vein, artery, or other portion of the body containing fluid. Embodiments of the analyte sensors of the subject disclosure may be configured to automatically monitor the level of the analyte over a time period which may range from minutes, hours, days, weeks, or longer, e.g., 14 days or longer, such as 21 days or 30 days or more.

Embodiments of the present disclosure relate to analyte detection/monitoring systems and devices which utilize analyte sensors including single-sided and double-sided analyte sensors wherein at least some of the electrodes of the sensor are in a stacked configuration, or are in a side-by-side configuration, and in some embodiments a sensor may have some electrodes side by side on a substrate surface, and at least one other electrode on the opposing side of the substrate which may be side by side if more than one or layered one on top of the other on the opposing substrate surface, or a combination thereof.

Embodiments of the present disclosure relate to analyte detection/monitoring systems and devices which utilize one or more sensor connectors, e.g., one or more rivets, to attach an analyte sensor having one or more electrodes to an electronics unit. Also provided, are systems and devices which utilize one or more conductive sensor connectors, e.g., one or more conductive rivets, to electrically connect an analyte sensor having one or more electrodes to an electronics unit, e.g., by electrically connecting one or more electrodes disposed on a first surface of the analyte sensor with one or more electrical contacts disposed on a second surface of the analyte sensor or a surface of the electronics unit. Methods of making and using the analyte detecting/monitoring systems and devices, as well as kits provided in connection with same, are disclosed herein. In addition, the present disclosure provides analyte sensors and analyte sensor precursors along with methods of making and using the same.

Sensor Connectors for Attaching an Analyte Sensor to an Electronics Unit

One or more sensor connectors may be utilized to attach an analyte sensor such as a glucose sensor having one or more electrodes to an electronics unit such as a sensor control unit of an analyte detection/monitoring system. Such sensor connectors may physically connect, electrically connect, or both physically and electrically connect the analyte sensor and the electronics unit. For example, where the analyte sensor includes at least an insulative base layer, an electrode, and an insulative layer, as described in greater detail below, the one or more sensor connectors may physically connect one or more of the insulative base layer, the electrode, and the insulative layer to the electronics unit. Where the analyte sensor includes a plurality of insulative layers and electrodes, more than one of the insulative layers and/or electrodes may be physically connected to the electronics unit via one or more sensor connectors. Where a connection that is both physical and electrical is provided, one or more conductive sensor connectors physically and electrically connects an electrode of the sensor to an electronics unit, e.g., by physically contacting both the electrode and an electrical contact of the electronics unit.

Regardless of the configuration of a sensor, e.g., whether it be single sided or double sided as described in greater detail below, a sensor connector may be used to physically or electrically, or physically and electrically connect the sensor, and more particularly the electrical contacts of the sensor, with conductive contacts of a sensor electronics unit. In many embodiments, the sensor is at least partially inserted into the body of a user (i.e., in vivo), and the sensor control unit is positioned outside the body (i.e., ex-vivo).

Suitable sensor connectors for use in the disclosed embodiments may take a variety of forms, including, but not limited to: rivets, clamps, screws, nails, pins, posts, vias, other connectors or attachment mechanisms known in the art, and combinations thereof.

Sensor connectors, e.g., rivets, suitable for use in connection with the present disclosure may be made from a variety of suitable materials depending on the particular application and the materials to be connected, e.g., joined. For example, where the sensor connector is one which physically connects the analyte sensor and the electronics unit, the sensor connector, e.g., rivet, may be made from any suitable non-conductive material, e.g, polycarbonate, acrylonitrile-butadiene-styrene (ABS), polycarbonate-acrylonitrile-butadiene-styrene (PC-ABS), polyethylene, and the like. It should be noted that conductive materials as described below may also be used to physically connect an analyte sensor and an electronics unit without electrically connecting the analyte sensor and the electronics unit or sensor control unit. Where the sensor connector is a conductive sensor connector which physically and electrically connects the analyte sensor and the electronics unit or sensor control unit, the conductive sensor connector, e.g., conductive rivet, may be made from any suitable conductive material, e.g., a metallic conductive material (e.g., gold, silver, platinum, aluminum, copper, brass, etc., or tin-plated or gold-plated versions thereof), carbon, or a conductive polymer (e.g., a conductive carbon polymer).

For embodiments utilizing a rivet, e.g., a conductive or non-conductive rivet, connection via the rivet may be made, for example, by inserting the rivet through a hole in a component of the analyte sensor, e.g., an electrode, an insulative base substrate or an insulative layer, and through a hole in a component of the electronics unit, e.g., a PCB or an electrical contact, followed by deformation of the rivet and expansion at the buck-tail end as a result of the application of force to the rivet head which joins the analyte sensor and the electronics unit to provide a physical and/or electrical connection between a component of the analyte sensor and the electronics unit. Application of the rivet may be accomplished using any of a variety of riveting processes known to those of ordinary skill in the art. For example, a spiral forming, impact forming or orbit forming process may be utilized.

In addition to providing a physical and/or electrical connection, the sensor connector, e.g., a rivet, may provide alignment or registration between an analyte sensor and an electronics unit, e.g., a PCB of an electronics unit. In addition, use of a sensor connector, e.g., a rivet, allows for a relatively low temperature connection or attachment process. Such a process may be beneficial when compared with a higher temperature process which has the potential to negatively affect the sensor materials and/or sensing chemistry. For example, connecting a sensor with an electronics unit using an adhesive, such as ACF (anisotropic conductive film) or ACA (anisotropic conductive adhesive) may require high temperatures to create a bond. Accordingly, embodiments of the present disclosure which utilize a sensor connector, e.g., a rivet, attachment mechanism provides advantages over other sensor attachment mechanisms and methods.

Figure 15M:
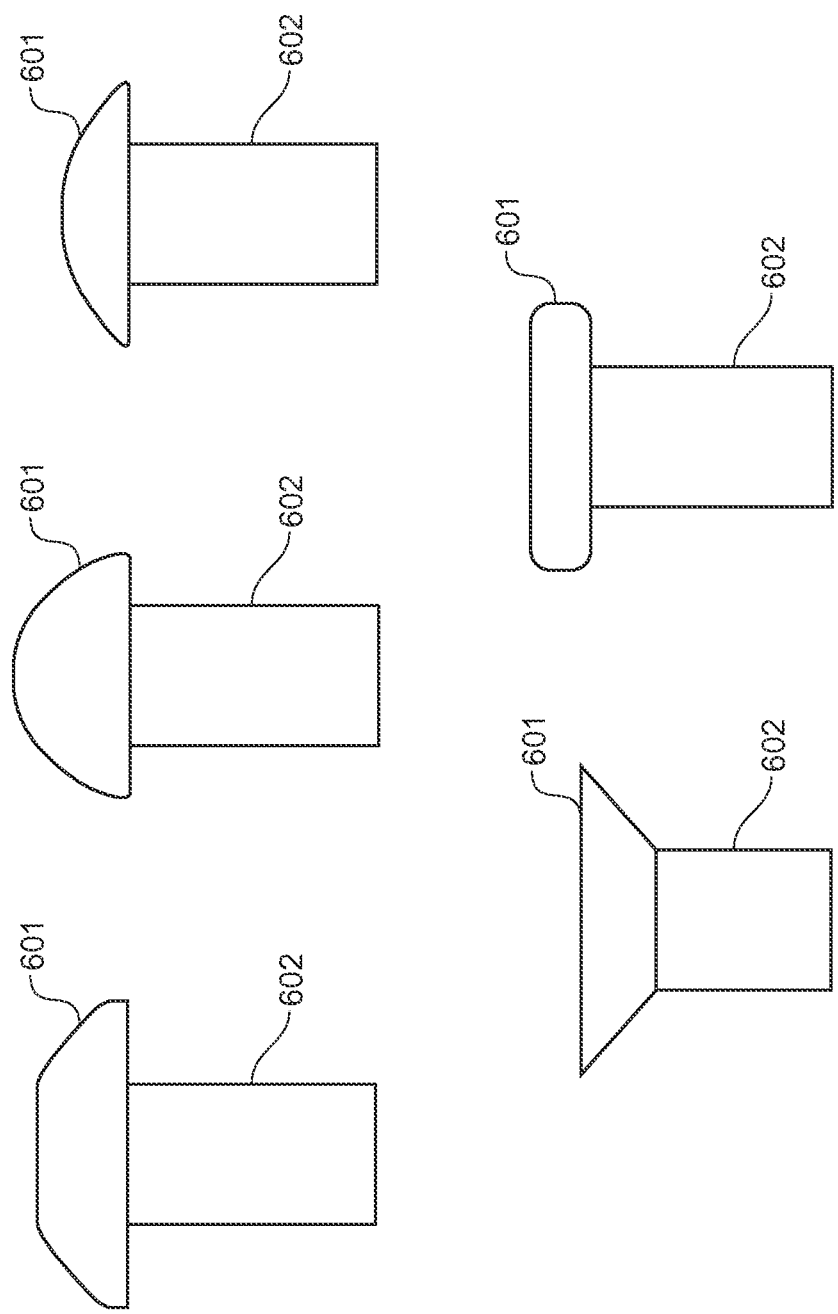
FIG. 15M shows side views of various rivet embodiments which may be used in connection with the present disclosure.

An embodiment of a sensor connector is a rivet connector. A rivet connector includes a head portion and a body or shaft portion terminating at a buck-tail end opposite the head portion, and in some embodiments includes a head portion at a first end and a second head portion at a second end (e.g., as a result of deformation of the buck-tail end during application of the rivet), and an intermediate body portion therebewteen. Exemplary rivet connectors are shown at FIGS. 15A-15M. FIGS. 15A-15C show an embodiment which includes a head portion and body portion, but as noted above a second head may also be included. Rivet 600 includes a head 601 and a shaft 602 positioned, for example, perpendicular thereto. The angle formed by the head 601 and shaft 602 is depicted as 90 degrees in FIGS. 15A-15C, but may range from 0 to 180 degrees, for example, it may be 10 degrees, 20 degrees, 30 degrees, 40 degrees, 50 degrees, 60 degrees, 70 degrees, 80 degrees, 90 degrees, 100 degrees, 110 degrees, 120 degrees, 130 degrees, 140 degrees, 150 degrees, 160 degrees, 170 degrees, 180 degrees or an increment thereof. In some embodiments, the angle formed by the head and shaft is between 90 degrees and 10 degrees, e.g., between 80 degrees and 10 degrees, between 70 degrees and 10 degrees, between 60 degrees and 10 degrees, between 50 degrees and 10 degrees, between 40 degrees and 10 degrees, between 30 degrees and 10 degrees or between 20 degrees and 10 degrees.

FIGS. 15D-15F show an embodiment, which like FIGS. 15A-15C, includes a head 601 and shaft 602. In this embodiment, the angle (indicated at 604), formed by the head 601 and shaft 602 is less than 90 degrees. Such an embodiment allows room for compression of the rivet head 601, e.g., during deformation of the rivet as a result of the application of force to rivet head 601 during application of the rivet 600, for example, to an analyte sensor and an electronics unit.

FIGS. 15G-15I show an embodiment, which like FIGS. 15A-15C, includes a head 601 and shaft 602. The rivet 600 is shown with an optional partial hole or lumen 603 opposite the head and extending at least partially through the shaft 602. Partial hole 603 allows for expansion or flaring of the shaft 602 at the end opposite the head 601 upon deformation of the rivet, e.g., as a result of the application of force to head 601 during application of the rivet 600, for example, to an analyte sensor and an electronics unit. This flaring facilitates connection of the analyte sensor and the electronics unit via the rivet as a result of contact between the flared rivet end and an area of the component of the analyte sensor or electronics unit adjacent the hole through which the rivet is inserted. FIGS. 15G-15I also show the angle 604 formed by the head 601 and shaft 602 is less than 90 degrees as discussed above. While partial hole or lumen 603 is depicted as terminating at a point at an end opposite the opening of the hole or lumen, many other configurations are possible. For example, the partial hole or lumen 603 could have a rectangular or cylindrical shape. In addition, in some embodiments, a hole or lumen may extend completely through the rivet.

FIGS. 15J-15L show an embodiment, which includes both an optional partial hole or lumen 603 opposite the head 601 and extending at least partially through the shaft 602 as discussed above and a configuration in which the angle 604 formed by the head 601 and shaft 602 is less than 90 degrees as discussed above. In addition, FIGS. 15J-15L show an optional beveled end 605 of shaft 602 at the end opposite head 601.

The sensor connector rivet head can be a round head rivet, flat head rivet, brazier head rivet, countersunk head rivet, universal rivet, or other construction. Exemplary rivets which may be used as sensor connector rivets are shown at FIG. 15M. In some embodiments, a conductive rivet which may be used as a sensor connector rivet includes one or more conductive portions and one or more non-conductive portions. For example, in some embodiments, a sensor connector rivet includes a conductive head and an insulative shaft (or vice versa). In some embodiments, a conductive rivet includes a conductive center core with non-conductive material positioned external to the conductive center core.

In some embodiments, the rivet head 601 contacts a sensor electronics unit and therefore includes an electronics contacting portion, and the shaft contacts a sensor and therefore includes a sensor contacting portion. The shaft 602 connects to a sensor, and in many embodiments connects by engagement through a hole or via of a sensor.

In other embodiments, the rivet head 601 contacts a sensor and therefore includes a sensor contacting portion, and the shaft contacts a sensor electronics unit and therefore includes a sensor electronics contacting portion. The shaft 602 connects to a sensor electronics unit, and in many embodiments connects by engagement through a hole or via of a sensor electronics unit.

Shaft 602 may have a uniform width, or may be variable at least along some of its length, e.g., as shown in FIGS. 15J-15L, wherein the shaft end opposite the rivet head 601 has a beveled end or edge 605. Some embodiments include a shaft that has a continually reduced width along its entire length from the head contacting end to its opposing end, or vice versa. FIGS. 15J-15L show a narrowing shaft end relative to the width of the rest of the shaft, at the shaft end that is opposite the shaft head contacting end. This end may alternatively be flared relative to the width of the rest of the shaft.

A sensor connector rivet may be rigid or may be flexible. In some embodiments, a rivet is compressible. A rivet may include some rigid portions and some compressible portions.

A sensor connector rivet may be solid or partially open, for example as described above with reference to FIGS. 15G-15I and 15J-15L, wherein the sensor connector rivet includes an optional partial hole or lumen 603 opposite the head and extending at least partially through the shaft 602. In such instances, the diameter of the partial hole or lumen may be, for example, from about 0.018 in to about 0.022 in, e.g., about 0.020 in. The hole or lumen depth may be, for example, from about 0.032 in to about 0.038 in, e.g., about 0.035 in.

Exemplary sensor connector rivet dimensions may be as follows: the rivet head may have a diameter of about 0.110 in to about 0.134 in, e.g., about 0.122 in; the rivet head may have a head thickness of about 0.018 in to about 0.022 in, e.g., 0.020 in; the rivet shaft may have a shaft length of about 0.056 in to about 0.070 in e.g., about 0.063 in; and the rivet shaft may have a diameter of about 0.035 to about 0.043, e.g., about 0.039 in. One of ordinary skill in the art will understand that these dimensions may be adjusted, e.g., to accommodate changes in analyte sensor and/or electronics unit dimensions. In addition, while the figures depict a rivet having a round rivet head and a generally cylindrical shaft, one of ordinary skill in the art will recognize that other shapes and configurations may be utilized.

An analyte sensor and an associated sensor electronics unit as described herein may be provided to a user of the sensor or a health care provider in several different configurations prior to insertion of the analyte sensor or a portion thereof in the user. For example, the analyte sensor may be provided attached to the sensor electronics unit via one or more sensor connectors, e.g., one or more rivets. In some embodiments, the analyte sensor and the sensor electronics unit may be provided separately, i.e., unattached, with one or both of the analyte sensor and the sensor electronics unit including one or more sensor connectors, e.g., a rivet positioned in a through hole or via in the analyte sensor and/or the sensor electronics unit. The analyte sensor and the sensor electronics unit may then be connected via the one or more sensor connectors either prior to or during insertion of the analyte sensor. In some embodiments, the analyte sensor and the sensor electronics unit may be provided separately with one or more sensor connectors also provided separately. The analyte sensor and sensor electronics unit can then be connected using the one or more sensor connectors, e.g., prior to or during insertion. In accordance with the above configurations, one or more of the analyte sensor, the sensor electronics unit and the one or more sensor connectors may be packaged separately or together.

Single-Sided Analyte Sensors Attached or Attachable to Electronics Units

The sensor connectors described herein can be used to connect many different types of sensors to sensor electronic units. Sensors include wire sensors and planar sensors. Wire sensors generally include a substrate (dielectric material) and electrodes (conductive material) and may include a core conductive wire that may be a working electrode, and one or more other conductive wires which may wrapped or coiled around at least a length of the core wire and serve as a reference electrode, counter electrode or reference/counter electrode. For exemplary purposes, electrochemical planar sensors are primarily described, where such description is in no way intended to limit the invention.

In some embodiments, the present disclosure provides an analyte detection/monitoring device including a single-sided analyte sensor attached via one or more sensor connectors, e.g., one or more rivets, to an electronics unit such as a sensor control unit, e.g., to a printed circuit board of an electronics unit or sensor control unit. As used herein, the term "single-sided analyte sensor" refers to an analyte sensor having one or more electrodes which may include, e.g, a conductive trace, positioned on one side of an at least generally planar insulative base substrate with or without an intermediary layer and no electrodes positioned on the opposing side of the insulative base substrate with or without an intermediary layer. Such sensors may have a stacked configuration, e.g., alternating conductive and insulative layers, or a side-by-side configuration, but in any event all of the electrodes and their respective conductive traces are on the same side of the insulating base substrate. In other words, the one or more electrodes may be provided on the same side of the insulative base substrate in either a layered or co-planar manner.

Embodiments of a single-sided, stacked sensor configuration which may be utilized in connection with the present disclosure are described, for example, in US Application No. 2011/0021889, the disclosure of which is incorporated by reference herein in its entirety and for all purposes.

The use of a sensor connector as described herein, e.g., a rivet, as a mechanism for attachment of an analyte sensor to an electronics unit, such as a sensor control unit, e.g., to a PCB of the sensor control unit, may result in improved attachment of the analyte sensor to the sensor control unit as compared with other attachment methods, e.g., the use of one or more adhesives. As discussed herein, the sensor connector, e.g., rivet, may be made from a variety of suitable materials depending on the particular embodiment. For example, is some embodiments, the sensor connector, e.g., rivet, physically connects the single-sided analyte sensor and the electronics unit. In other embodiments, the sensor connector, e.g., rivet, physically and electrically connects the single-sided analyte sensor and the electronics unit. Where the sensor connector, e.g., rivet, physically connects the analyte sensor and the electronics unit, the sensor connector, e.g., rivet, may be made from any suitable conductive or non-conductive material. Where the sensor connector, e.g., a conductive rivet, physically and electrically connects the single-sided analyte sensor and the electronics unit, the sensor connector, e.g., a conductive rivet, may be made from any suitable conductive material, e.g., copper. In some embodiments, the sensor connector, e.g., a conductive rivet, may conduct an electrical signal from an electrode, e.g. a conductive trace of an electrode, positioned on one side of the single-sided analyte sensor to the other side of the single-sided analyte sensor, e.g., for electrical connection with a PCB to which the single-sided analyte sensor is attached. Where a plurality of electrodes is present, one or more of the plurality of electrodes may be electrically connected to the PCB via a corresponding conductive sensor connector, e.g., a conductive rivet. For example, an analyte sensor having three electrodes may include 1, 2 or 3 conductive sensor connectors, e.g., rivets; an analyte sensor having four electrodes may include 1, 2, 3 or 4 conductive sensor connectors, e.g., conductive rivets; etc. Additional non-conductive and conductive sensor connector, e.g., rivet, materials are discussed herein.

Double-Sided Analyte Sensors Attached or Attachable to Electronics Units

In some embodiments, an analyte detection/monitoring device including a double-sided analyte sensor attached via one or more sensor connectors, e.g., rivets, to an electronics unit, such as a sensor control unit, e.g., to a PCB of the sensor control unit, is provided. As used herein, the term "double-sided analyte sensor" refers to an analyte sensor having one or more electrodes which may include, e.g., a conductive trace, positioned on one side of an at least generally planar insulative base substrate with or without an intermediary layer and one or more electrodes positioned on the opposite side of the insulative base substrate with or without an intermediary layer. In a double-sided analyte sensor, at least one electrode, e.g., a conductive trace of at least one electrode, is at least partially exposed for electrical connection on one face of the at least generally planar insulative base substrate and at least one electrode, e.g., a conductive trace of at least one electrode, is at least partially exposed on the opposite face of the at least generally planar insulative base substrate for electrical connection. Such sensors may have a stacked configuration, e.g., alternating conductive and insulative layers, or a side-by-side configuration. In other words, the one or more electrodes may be provided on opposite sides of the at least generally planar insulative base substrate in either a layered or co-planar manner.

Figure 2:
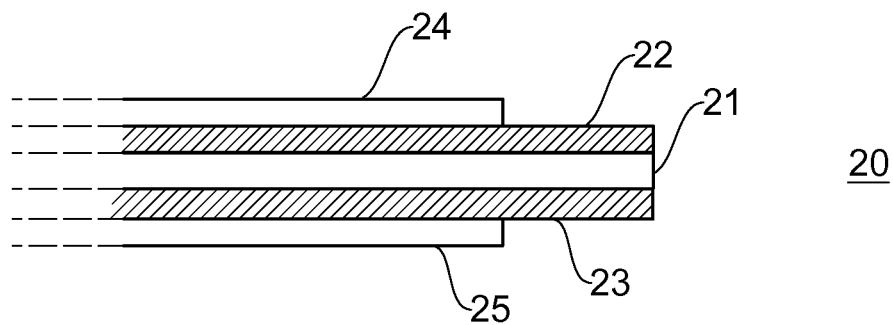
FIGS. 2-4 show cross-sectional views of distal portions of embodiments of double-sided analyte sensors which may be utilized in connection with embodiments of the present disclosure.

Embodiments of a double-sided, stacked sensor configuration which may be utilized in connection with the present disclosure are described below with reference to FIGS. 2-4. FIG. 2 shows a cross-sectional view of a distal portion of a double-sided analyte sensor 20. Analyte sensor 20 includes an at least generally planar insulative base substrate 21, e.g., an at least generally planar dielectric base substrate, having a first conductive layer 22 which substantially covers the entirety of a first surface area, e.g., the top surface area, of insulative substrate 21, i.e., the conductive layer substantially extends the entire length of the substrate to the distal edge and across the entire width of the substrate from side edge to side edge. A second conductive layer 23 substantially covers the entirety of a second surface, e.g., the bottom side, of insulative base substrate 21. However, one or both of the conductive layers may terminate proximally of the distal edge and/or may have a width which is less than that of insulative substrate 21 where the width ends a selected distance from the side edges of the substrate, which distance may be equidistant or vary from each of the side edges.

One of the first or second conductive layers, e.g., first conductive layer 22, may be configured to include the sensor's working electrode. The opposing conductive layer, here, second conductive layer 23, may be configured to include a reference and/or counter electrode. Where conductive layer 23 serves as either a reference or counter electrode, but not both, a third electrode may optionally be provided either on a surface area of the proximal portion of the sensor (not shown), on a separate substrate, or as an additional conductive layer positioned either above or below conductive layer 22 or 23 and separated from those layers by an insulative layer or layers. For example, in some embodiments, where analyte sensor 20 is configured to be partially implanted, conductive layer 23 may be configured to include a reference electrode and a third electrode (not shown) and present only on a non-implanted proximal portion of the sensor may be configured to include the sensor's counter electrode.

A first insulative layer 24 covers at least a portion of conductive layer 22 and a second insulative layer 25 covers at least a portion of conductive layer 23. In one embodiment, at least one of first insulative layer 24 and second insulative layer 25 does not extend to the distal end of analyte sensor 20 leaving an exposed region of the conductive layer or layers.

Figure 3:
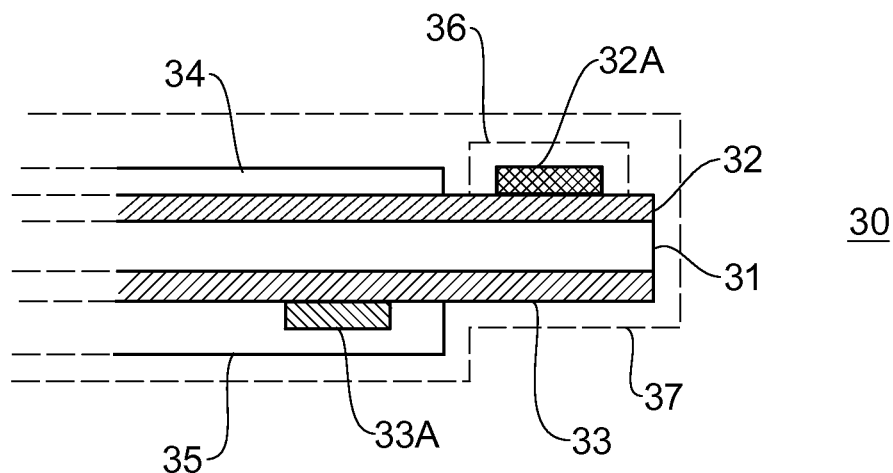

FIG. 3 shows a cross-sectional view of a distal portion of a double-sided analyte sensor 30 including an at least generally planar insulative base substrate 31, e.g., an at least generally planar dielectric base substrate, having a first conductive layer 32 which substantially covers the entirety of a first surface area, e.g., the top surface area, of insulative substrate 31, i.e., the conductive layer substantially extends the entire length of the substrate to the distal edge and across the entire width of the substrate from side edge to side edge. A second conductive layer 33 substantially covers the entirety of a second surface, e.g., the bottom side, of insulative base substrate 31. However, one or both of the conductive layers may terminate proximally of the distal edge and/or may have a width which is less than that of insulative substrate 31 where the width ends a selected distance from the side edges of the substrate, which distance may be equidistant or vary from each of the side edges.

In the embodiment of FIG. 3, conductive layer 32 is configured to include a working electrode which includes a sensing component or layer 32A disposed on at least a portion of the first conductive layer 32 as shown and as discussed in greater detail below. While a single sensing component or layer 32A is shown, it should be noted that in other embodiments a plurality of spatially separated sensing components or layers may be utilized.

In the embodiment of FIG. 3, conductive layer 33 is configured to include a reference electrode which includes a secondary layer of conductive material 33A, e.g., Ag/AgCl, disposed over a distal portion of conductive layer 33.

A first insulative layer 34 covers a portion of conductive layer 32 and a second insulative layer 35 covers a portion of conductive layer 33. First insulative layer 34 does not extend to the distal end of analyte sensor 20 leaving an exposed region of the conductive layer where the sensing component or layer 32A is positioned. The insulative layer 35 on the bottom/reference electrode side of the sensor, may extend any suitable length of the sensor's distal section, i.e., it may extend the entire length of both of the primary and secondary conductive layers or portions thereof. For example, as illustrated in FIG. 3, bottom insulative layer 35 extends over the entire bottom surface area of secondary conductive material 33A but terminates proximally of the distal end of the length of the conductive layer 33. It is noted that at least the ends of the secondary conductive material 33A which extend along the side edges of the substrate 31 are not covered by insulative layer 35 and, as such, are exposed to the environment when in operative use.

Figure 4:
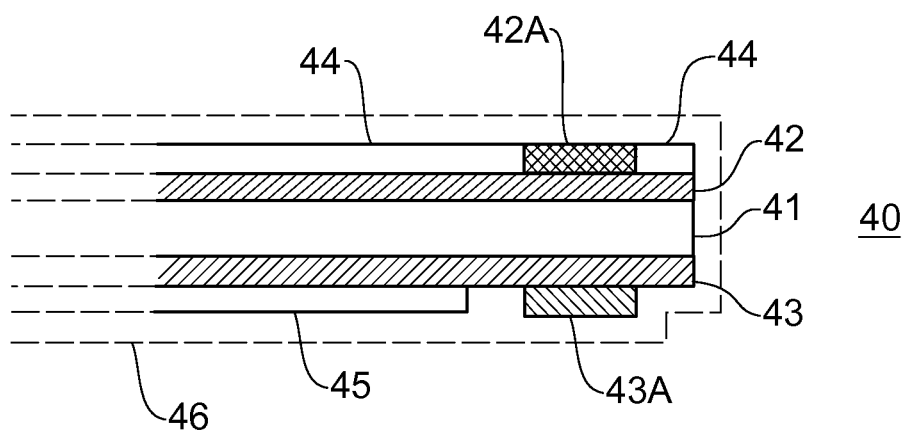

In an alternative embodiment, as shown in FIG. 4, insulative layer 44 on the working electrode side of an insulative base substrate 41 may be provided prior to sensing layer 42A whereby the insulative layer 44 has at least two portions spaced apart from each other on conductive layer 42. The sensing material 42A is then provided in the spacing between the two portions. More than two spaced apart portions may be provided, e.g., where a plurality of sensing components or layers is desired. Bottom insulative layer 45 has a length which terminates proximally of secondary conductive layer 43a on bottom primary conductive layer 43. Additional conducting and dielectric layers may be provided on either or both sides of the sensors, as described above.

While FIGS. 2-4 depict or are discussed herein as capable of providing the working and reference electrodes in a particular layered configuration, it should be noted that the relative positioning of these layers may be modified. For example, a counter electrode layer may be provided on one side of an insulative base substrate while working and reference electrode layers are provided in a stacked configuration on the opposite side of the insulative base substrate. In addition, a different number of electrodes may be provided than depicted in FIGS. 2-4 by adjusting the number of conductive and insulative layers. For example, a 3 or four electrode sensor may be provided.

One or more membranes, which may function as one or more of an analyte flux modulating layer and/or an interferent-eliminating layer and/or biocompatible layer, discussed in greater detail below, may be provided about the sensor, e.g., as one or more of the outermost layer(s). In certain embodiments, as illustrated in FIG. 3, a first membrane layer 36 may be provided solely over the sensing component or sensing layer 32A on the working electrode 32 to modulate the rate of diffusion or flux of the analyte to the sensing layer. For embodiments in which a membrane layer is provided over a single component/material, it may be suitable to do so with the same striping configuration and method as used for the other materials/components. Here, the stripe/band of membrane material 36 preferably has a width greater than that of sensing stripe/band 32A. As it acts to limit the flux of the analyte to the sensor's active area, and thus contributes to the sensitivity of the sensor, controlling the thickness of membrane 36 is important. Providing membrane 36 in the form of a stripe/band facilitates control of its thickness. A second membrane layer 37, which coats the remaining surface area of the sensor tail, may also be provided to serve as a biocompatible conformal coating and provide smooth edges over the entirety of the sensor. In other sensor embodiments, as illustrated in FIG. 4, a single, homogenous membrane 46 may be coated over the entire sensor surface area, or at least over both sides of the distal tail portion. It is noted that to coat the distal and side edges of the sensor, the membrane material may have to be applied subsequent to singulation of the sensor precursors. In some embodiments, the analyte sensor is dip-coated following singulation to apply one or more membranes. Alternatively, the analyte sensor could be slot-die coated wherein each side of the analyte sensor is coated separately.

Figure 5:
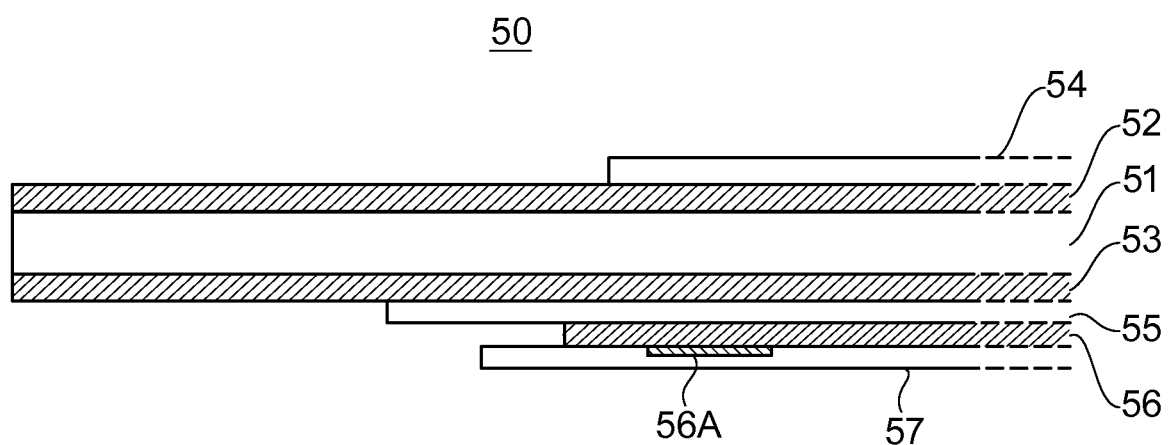
FIG. 5 shows a cross-sectional view of a distal portion of another embodiment of a double-sided analyte sensor which may be utilized in connection with embodiments of the present disclosure.

FIG. 5 shows a cross-sectional view of a distal portion of a double-sided analyte sensor 50 according to one embodiment of the present disclosure, wherein the double-sided analyte sensor includes an at least generally planar insulative base substrate 51, e.g., an at least generally planar dielectric base substrate, having a first conductive layer 52. A second conductive layer 53 is positioned on a first side, e.g., the bottom side, of insulative base substrate 51. While depicted as extending to the distal edge of the sensor, one or both of the conductive layers may terminate proximally of the distal edge and/or may have a width which is less than that of insulative substrate 51 where the width ends a selected distance from the side edges of the substrate, which distance may be equidistant or vary from each of the side edges. See, for example, the analyte sensor assembly 500, discussed in more detail below, wherein first and second conductive layers are provided which define electrodes, including, e.g., electrode traces, which have widths which are less than that of the insulative base substrate.

In the embodiment of FIG. 5, conductive layer 53 is configured to include a working electrode which includes a sensing component or layer (not shown) disposed on at least a portion of the conductive layer 53, which sensing component or layer is discussed in greater detail below. It should be noted that a plurality of spatially separated sensing components or layers may be utilized in forming the working electrode, e.g., one or more sensing "dots" or areas may be provided on the conductive layer 53.

In the embodiment of FIG. 5, conductive layer 56 is configured to include a reference electrode which includes a secondary layer of conductive material 56A, e.g., Ag/AgCl, disposed on a distal portion of conductive layer 56. Like conductive layers 52 and 53, conductive layer 56 may terminate proximally of the distal edge and/or may have a width which is less than that of insulative substrate 51 where the width ends a selected distance from the side edges of the substrate, which distance may be equidistant or vary from each of the side edges.

In the embodiment shown in FIG. 5, conductive layer 52 is configured to include a counter electrode. A first insulative layer 54 covers a portion of conductive layer 52 and a second insulative layer 55 covers a portion of conductive layer 53. First insulative layer 54 does not extend to the distal end of analyte sensor 50 leaving an exposed region of the conductive layer 52 which acts as the counter electrode. An insulative layer 55 covers a portion of conductive layer 53 leaving an exposed region of the conductive layer 53 where the sensing component or layer (not shown) is positioned. As discussed above, multiple spatially separated sensing components or layers may be provided in some embodiments. The insulative layer 57 on a first side, e.g., the bottom side of the sensor (in the view provided by FIG. 5), may extend any suitable length of the sensor's distal section, i.e., it may extend the entire length of both of conductive layers 56 and 56A or portions thereof. For example, as illustrated in FIG. 5, bottom insulative layer 57 extends over the entire bottom surface area of secondary conductive material 56A and terminates distally of the distal end of the length of the conductive layer 56. It is noted that at least the ends of the secondary conductive material 56A which extend along the side edges of the substrate 51 are not covered by insulative layer 57 and, as such, are exposed to the environment when in operative use.

As discussed previously herein, when manufacturing layered sensors, it may be desirable to utilize relatively thin insulative layers to reduce total sensor width. For example, with reference to FIG. 5, insulative layers 54, 55 and 57 may be relatively thin relative to insulative substrate layer 51. For example, insulative layers 54, 55 and 57 may have a thickness in the range of 20-25 μm while substrate layer 51 has a thickness in the range of 0.1 to 0.15 mm. However, during singulation of the sensors where such singulation is accomplished by cutting through two or more conductive layers which are separated by such thin insulative layers, shorting between the two conductive layers may occur. One method of addressing this potential issue is to provide one of the conductive layers, e.g., electrodes layers, at least in part as a relatively narrow electrode, including, e.g., a relatively narrow conductive trace, such that during the singulation process the sensor is cut on either side of the narrow electrode such that one electrode is cut without cutting through the narrow electrode. See, for example, sensor assembly 500 depicted in FIG. 6 in which working electrode 502 is provided at its distal end as a relatively thin electrode relative to reference electrode 504. In addition, one of the conductive layers may be spaced back from the other conductive layer at the distal end of the sensor. One of the sensors may extend, for example, to the distal tip of the sensor while the other terminates proximal to the distal tip of the sensor. In this manner, the sensor may be cut perpendicularly to the length of the sensor and across one of the conductive layers without cutting through two conductive layers separated by only a thin insulative layer, e.g., an insulative layer having a thickness from about 15 to 30 μm. In the embodiment depicted in FIG. 5 the reference electrode 56 is spaced back distally relative to the working electrode 53. However, this positioning could be reversed.

As discussed above, the use of a sensor connector, e.g., a rivet, as a mechanism for attachment of an analyte sensor to an electronics unit, such as sensor control unit, e.g., to a PCB of the sensor control unit, may result in improved attachment of the analyte sensor to the sensor control unit as compared with other attachment methods, e.g., the use of one or more adhesives. The sensor connector, e.g., a rivet, may be made from a variety of suitable materials depending on the particular embodiment. For example, is some embodiments, the sensor connector, e.g., a rivet, physically connects the double-sided analyte sensor and the electronics unit. In other embodiments, the sensor connector, e.g., rivet physically and electrically connects the double-sided analyte sensor and the electronics unit. Where the sensor connector, e.g., rivet physically connects the analyte sensor and the electronics unit, the sensor connector, e.g., rivet may be made from any suitable conductive or non-conductive material. Where the sensor connector, e.g., rivet physically and electrically connects the double-sided analyte sensor and the electronics unit, the sensor connector, e.g., rivet, may be made from any suitable conductive material, e.g., copper. In one such embodiment, the sensor connector, e.g., rivet, may conduct an electrical signal from an electrode, including, e.g., a conductive trace, positioned on one side of the double-sided analyte sensor to the other side of the double-sided analyte sensor, e.g., for electrical connection with a PCB to which the double-sided analyte sensor is attached. In this way, both sides of a double-sided analyte sensor may be electrically connected to the sensor control unit. Where a plurality of electrodes is present, one or more of the plurality of electrodes may be electrically connected to the PCB via a corresponding conductive sensor connector, e.g., a conductive rivet. For example, an analyte sensor having three electrodes may include 1, 2 or 3 conductive sensor connectors, e.g., conductive rivets; an analyte sensor having four electrodes may include 1, 2, 3 or 4 conductive sensor connectors, e.g., conductive rivets; etc. Additional non-conductive and conductive sensor connector, e.g., rivet, materials are discussed in greater detail above.

A double-sided analyte sensor may provide certain advantages over a single-sided analyte sensor. Specifically, by positioning electrodes, e.g., including conductive traces, on both sides of a dielectric base layer, a reduction in analyte sensor width can be achieved. For example, such a double-sided analyte sensor may have width of less than 0.5 mm, e.g., less than 0.3 mm. Additional descriptions of double-sided analyte sensors can be found, for example, in US Publication Nos. 2010/0230285 and 2011/0021889, the disclosure of each of which is incorporated by reference herein in its entirety and for all purposes.

Figure 6:
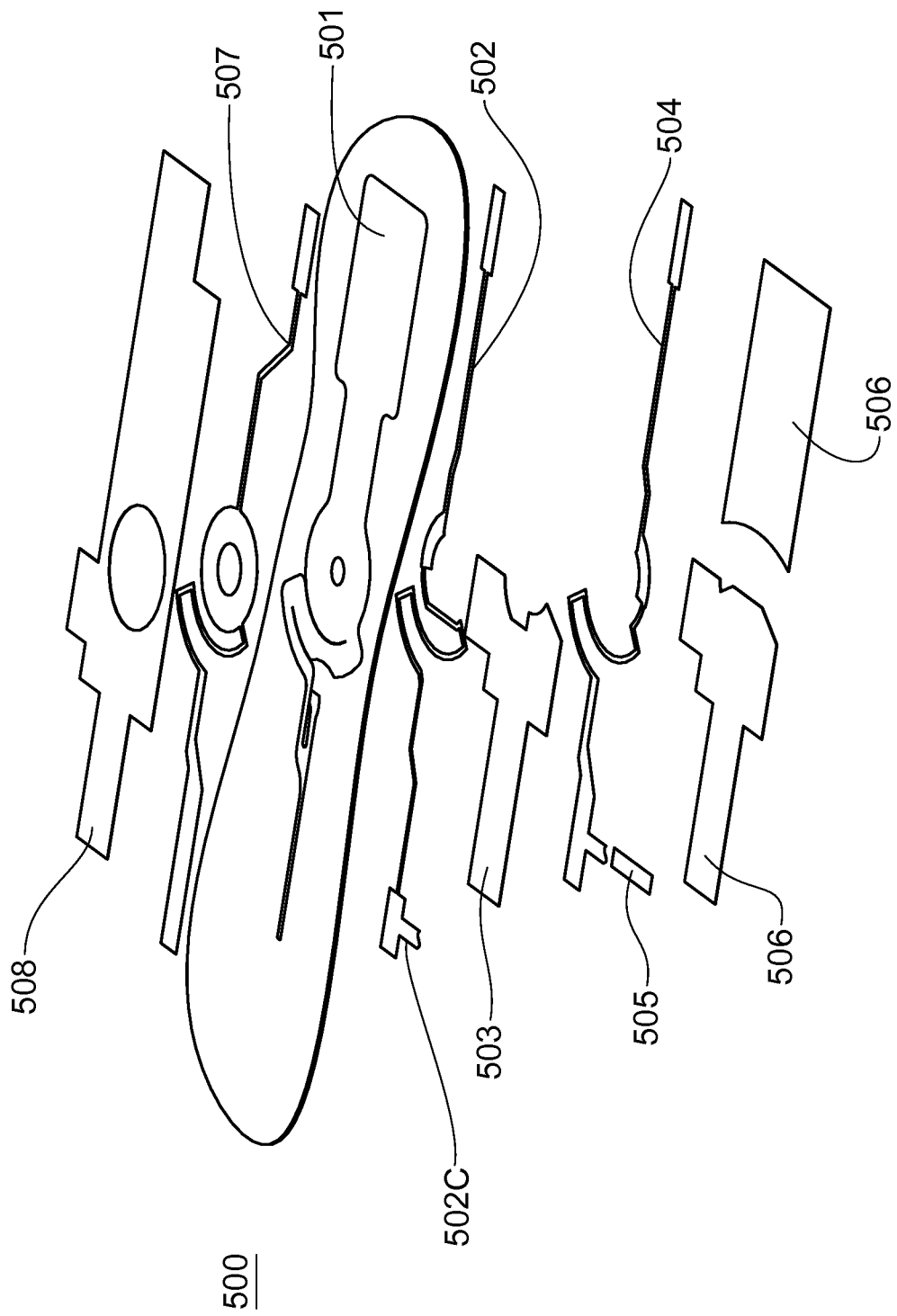
FIG. 6 provides an exploded view of an analyte sensor assembly according to one embodiment of the present disclosure.

Exemplary embodiments of a double-sided analyte sensor for use in connection with the disclosed devices, methods, systems and kits will now be described in greater detail with reference to FIGS. 6-14 which depict an analyte sensor assembly showing the various layers of the analyte sensor as they may be positioned in an analyte sensor sheet containing a plurality of analyte sensors prior to singulation of an individual analyte sensor. FIG. 6 provides an exploded view of an analyte sensor assembly 500 according to one embodiment of the present disclosure. Analyte sensor assembly 500 includes a Layer 0 in the form of a flexible insulative base substrate, e.g., a flexible dielectric substrate 501. The flexible dielectric substrate 501 may be made of any suitable dielectric material having the desired flexibility. For example, the flexible dielectric substrate 501 may be a clear, high-gloss, heat stabilized polyester film. Other suitable materials are provided below and still others may be readily identified by those of ordinary skill in the art.

Figure 8:
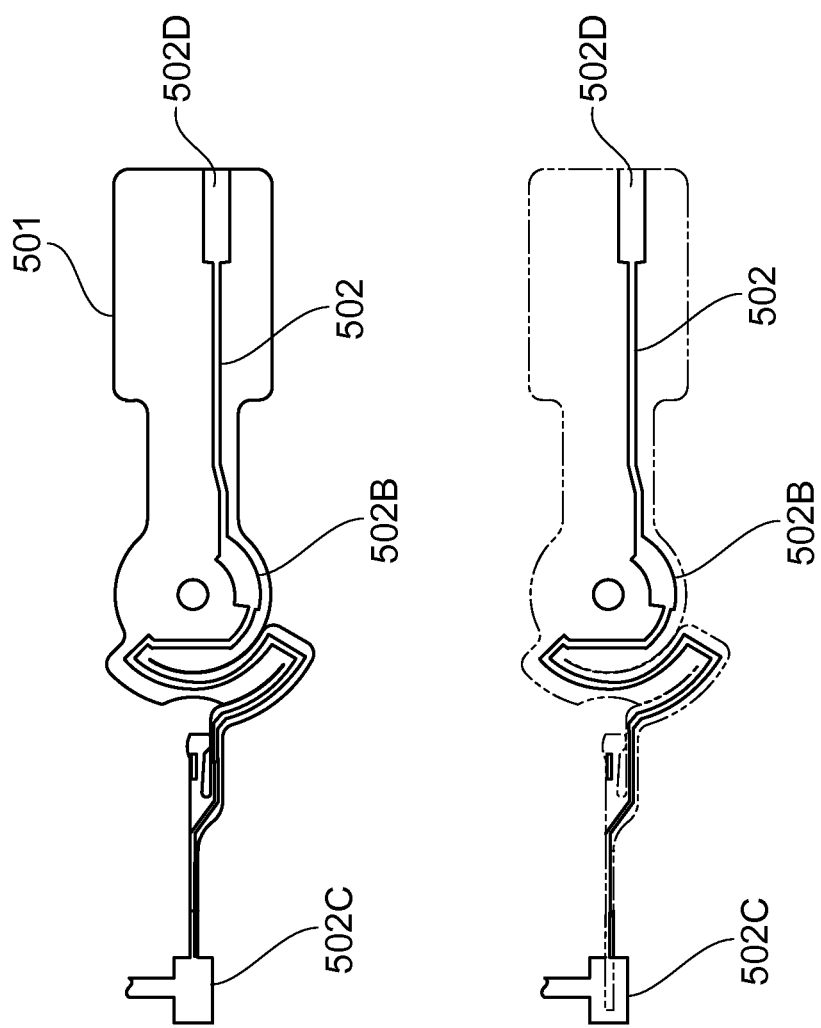
FIG. 8 shows a bottom view of a first sensor layer, a working electrode layer positioned on a dielectric substrate, of the analyte sensor assembly shown in FIG. 7.

Working electrode 502, including a working electrode trace, Layer 1, is positioned on flexible dielectric substrate 501. See, FIGS. 6 and 8. A variety of conductive materials may be used to form working electrode 502, and many such materials are known to those of ordinary skill in the art. A discussion of suitable materials is also provided below. In one embodiment, working electrode 502 is applied in the form of a carbon ink. FIG. 8 also depicts electrical contacts 502B, 502C and 502D. Electrical contact 502B is configured to provide an electrical connection with an electronics unit, such as sensor control unit, e.g., a PCB of a sensor control unit. Optional electrical contacts 502C and 502D may be utilized during the manufacturing process to test the functionality of the working electrode, and may be subsequently removed during singulation of the analyte sensor or not provided at all.

Figure 9:
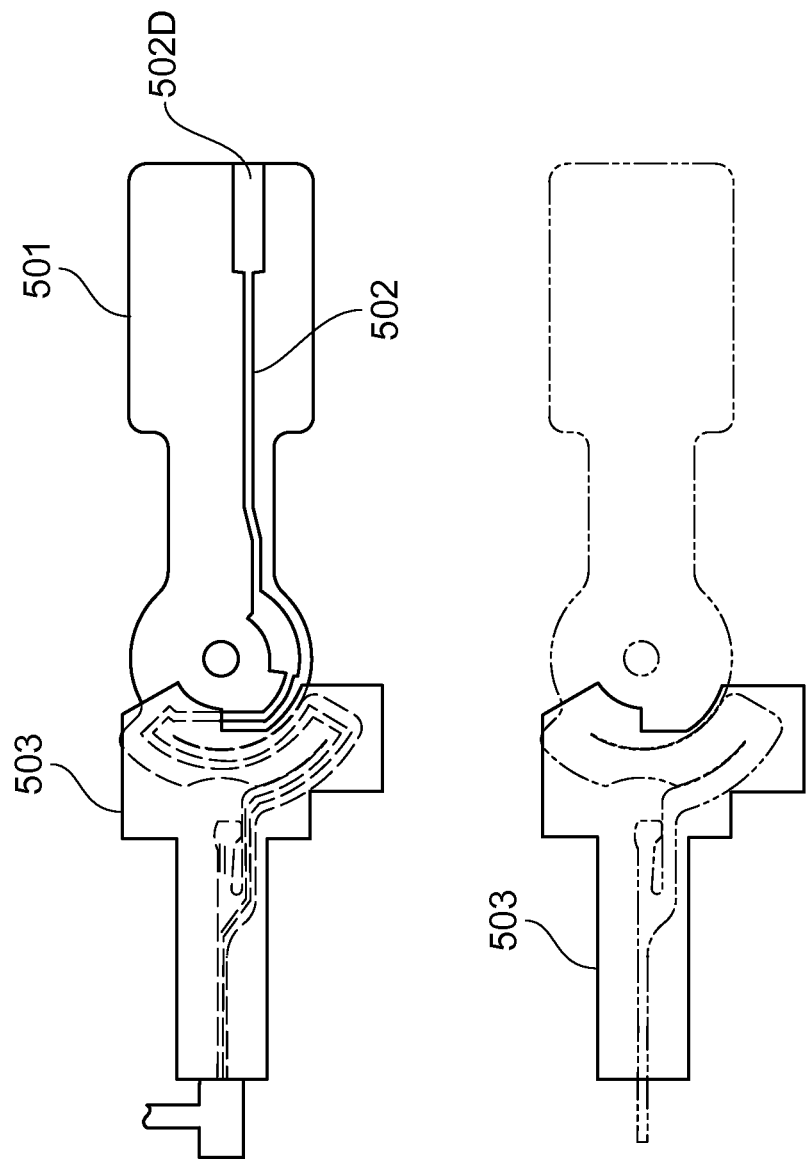
FIG. 9 shows a bottom view of a second sensor layer, a dielectric layer, covering a portion of the working electrode layer shown in FIG. 8.

A dielectric layer 503, Layer 2, is positioned to cover a portion of working electrode 502 as shown in FIGS. 6 and 9. In one embodiment, a suitable dielectric is a UV curable dielectric. Additional suitable dielectric materials are described below and others may be readily identified by those of ordinary skill in the art.

Figure 10:
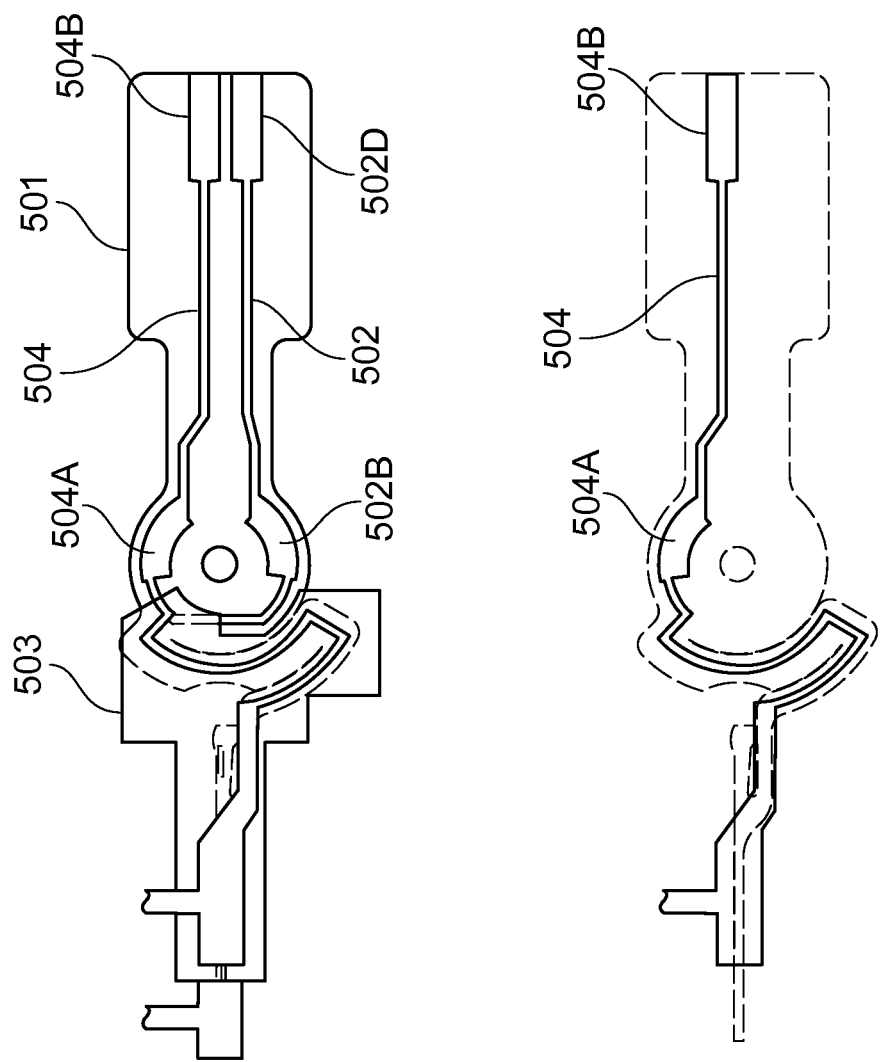
FIG. 10 shows a bottom view of a third sensor layer, a reference electrode layer, positioned over (relative to the plane of the page) the second sensor layer shown in FIG. 9.
Figure 11:
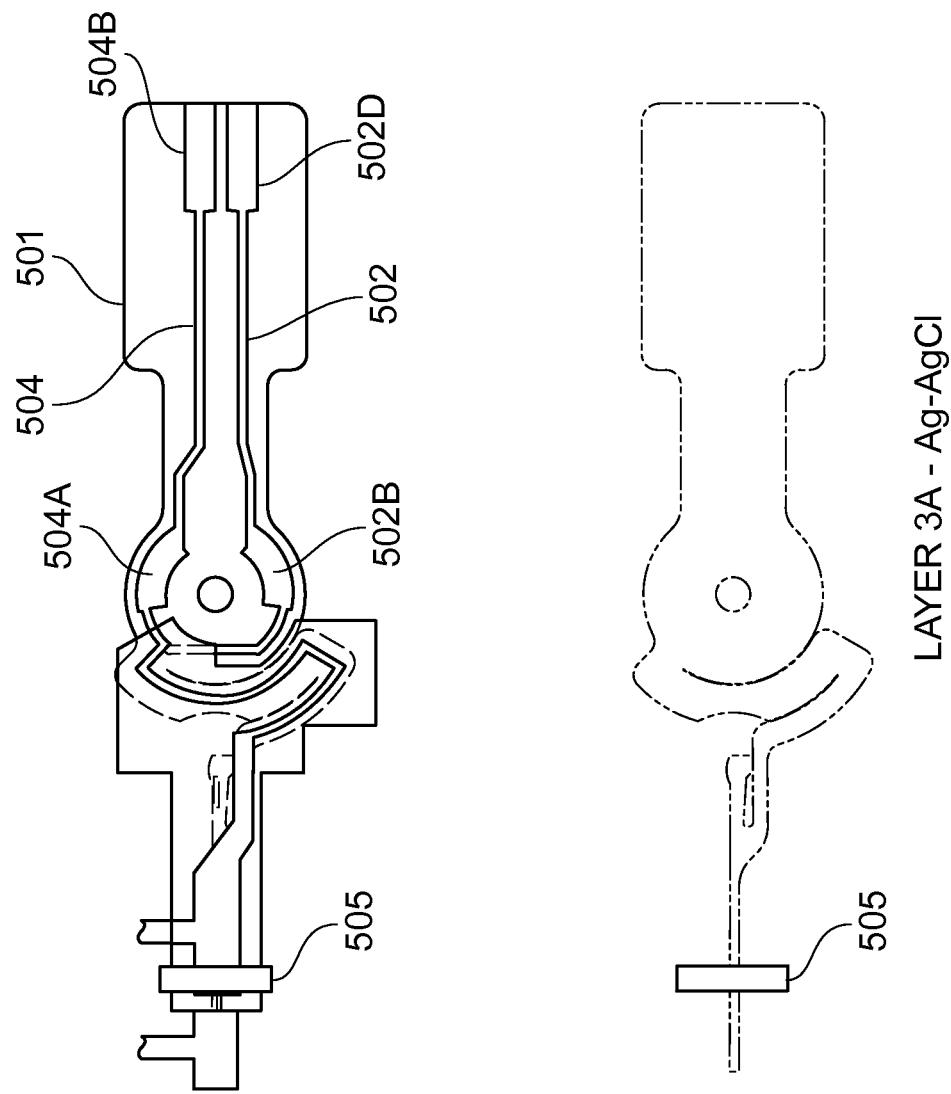
FIG. 11 shows a Ag/AgCl layer positioned on the reference electrode layer shown in FIG. 10.

Reference electrode 504, Layer 3, is positioned on dielectric layer 503 and flexible dielectric substrate 501 as shown in FIGS. 6 and 10. A variety of conductive materials may be used to form reference electrode 504, e.g., carbon ink, and many such materials are known to those of ordinary skill in the art. A discussion of suitable materials is also provided below. In addition, reference electrode 504 includes a Ag/AgCl layer 505, Layer 3A, applied to a portion thereof as depicted in FIGS. 6 and 11. Additional reference electrode materials known to those of ordinary skill in the art may be utilized in connection with the present disclosure. Also shown are electrical contacts 504A and 504B. Electrical contact 504A is configured to provide an electrical connection with an electronics unit, such as a sensor control unit, e.g., a PCB of a sensor control unit. Optional electrical contact 504B may be utilized during the manufacturing process to test the functionality of the reference electrode, and may be subsequently removed during singulation of the analyte sensor or not provided at all.

Figure 12:
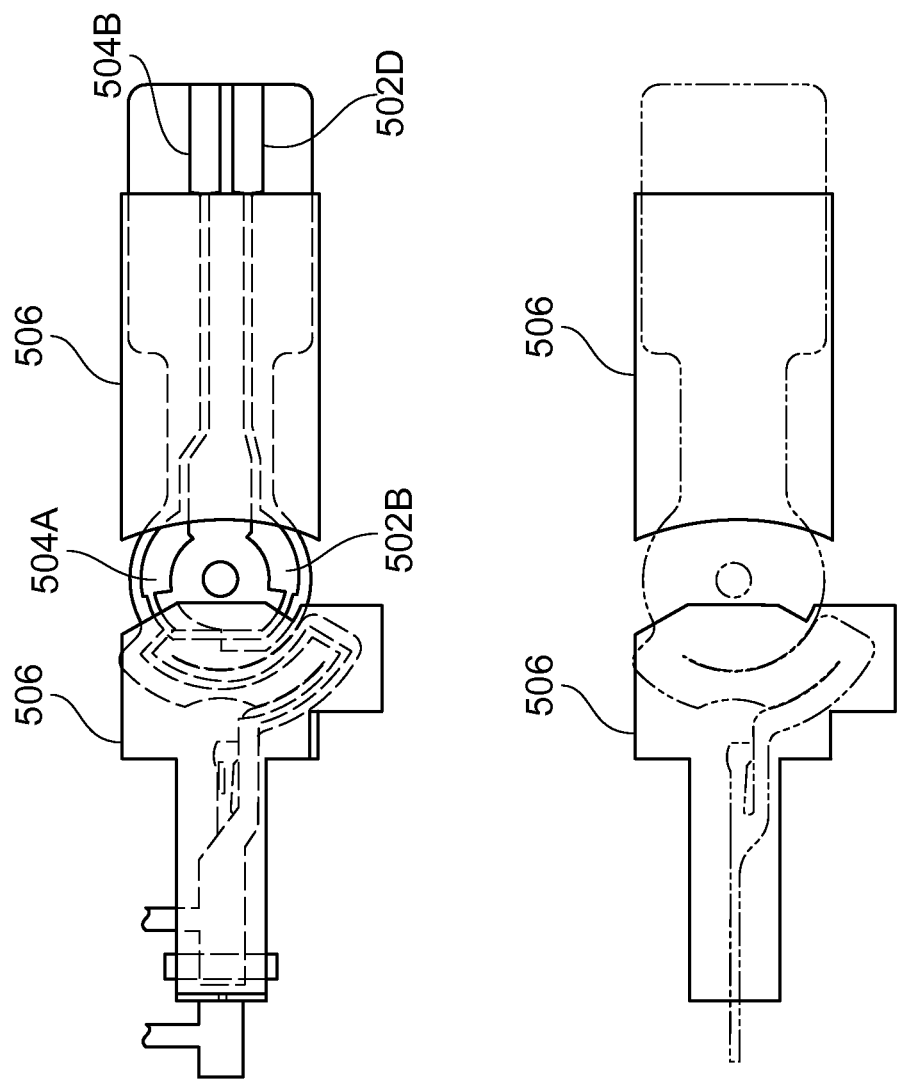
FIG. 12 shows a bottom view of a fourth sensor layer, a dielectric layer, positioned over (relative to the plane of the page) the Ag/AgCl layer and the working and reference electrode layers as shown in FIGS. 8-11.

A dielectric layer 506, Layer 4, is positioned over (relative to the plane of the page in FIG. 12) the Ag/AgCl layer and the working and reference electrode layers as shown in FIG. 12. As shown in FIG. 12, this layer may be applied in two separate parts, however, embodiments in which this dielectric layer is applied as a single part are also contemplated by the disclosure. In one embodiment, a suitable dielectric is a UV curable dielectric. Additional suitable dielectric materials are described below and others may be readily identified by those of ordinary skill in the art.

Figure 13:
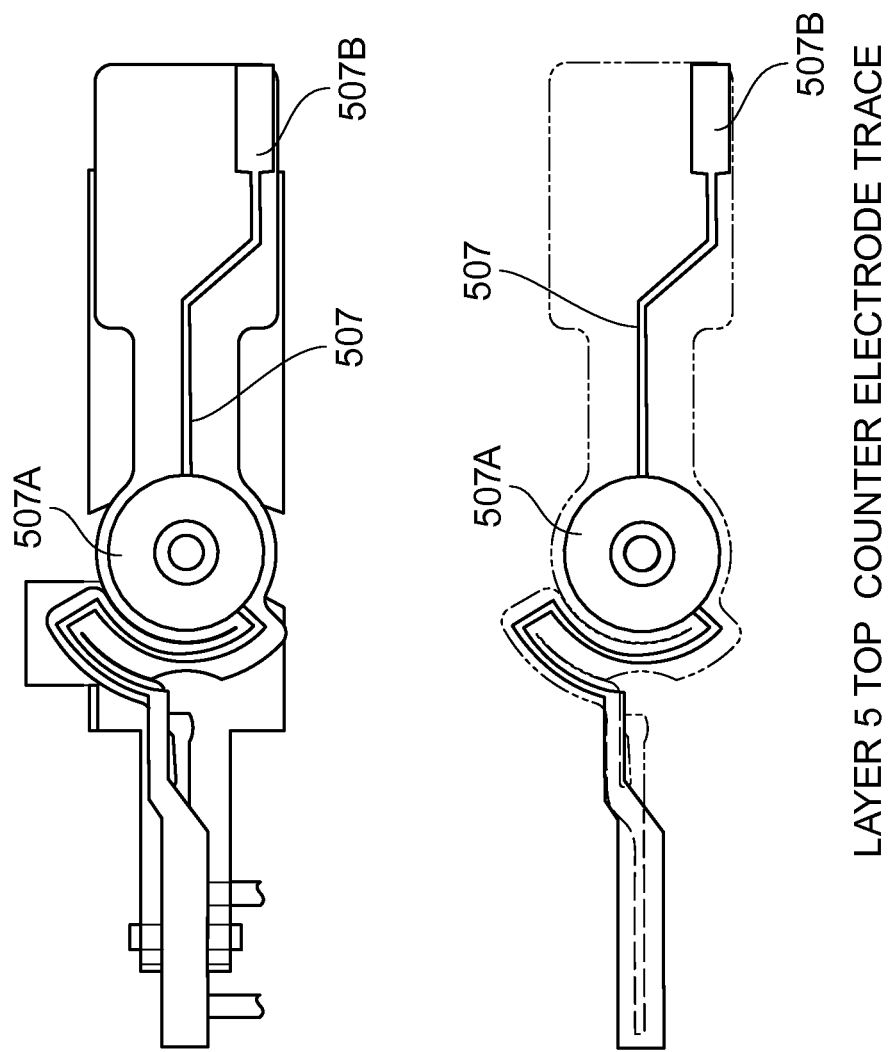
FIG. 13 shows a top view of a fifth sensor layer, a counter electrode layer, positioned over (relative to the plane of the page) the layers shown in FIGS. 8-12.

A counter electrode 507, Layer 5, is positioned on flexible dielectric substrate 501 on the opposite side of flexible dielectric substrate 501 as working electrode 502 as shown in FIG. 13. A variety of conductive materials may be used to form counter electrode 507, and many such materials are known to those of ordinary skill in the art. A discussion of suitable materials is also provided below. In one embodiment, counter electrode 507 is applied in the form of a carbon ink. Also shown are electrical contacts 507A and 507B. Electrical contact 507A is configured to provide an electrical connection with an electronics unit, such as a sensor control unit, e.g., a PCB of a sensor control unit. Optional electrical contact 507B may be utilized during the manufacturing process to test the functionality of the counter electrode, and may be subsequently removed during singulation of the analyte sensor.

Figure 14:
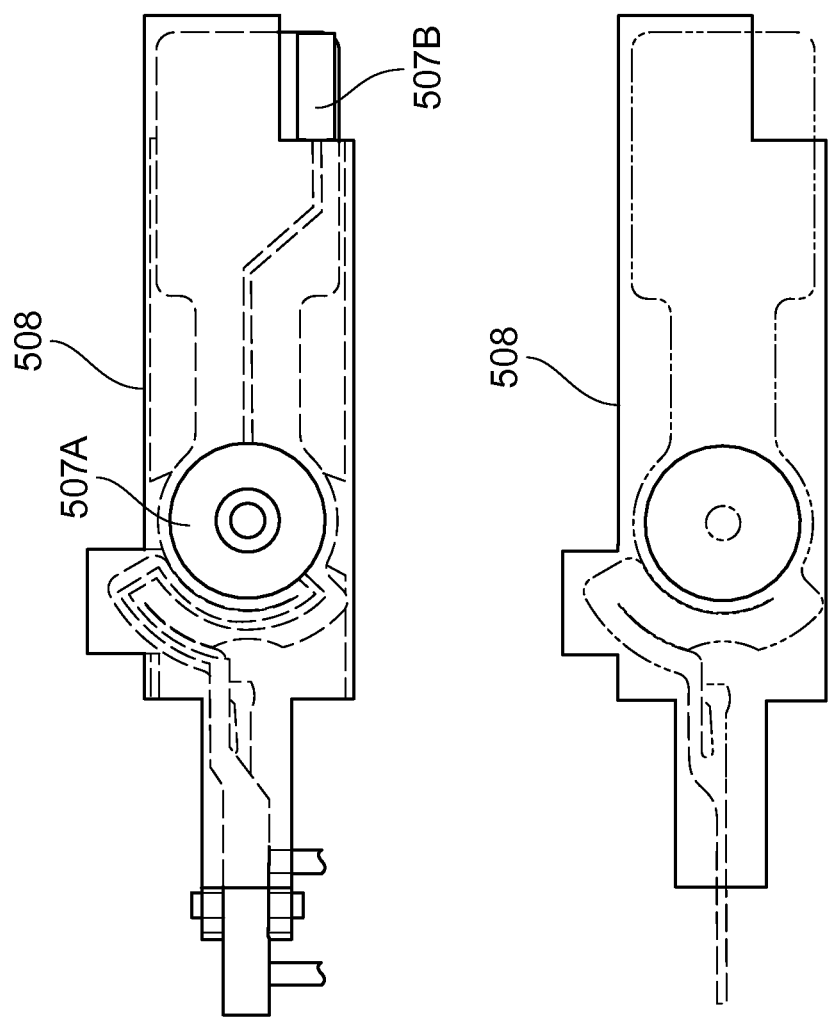
FIG. 14 shows a top view of a sixth sensor layer, a dielectric layer, positioned over (relative to the plane of the page) portions of the counter electrode layer shown in FIG. 13.

An additional dielectric layer 508, Layer 6, is applied over portions of counter electrode 507 as shown in FIG. 14. In one embodiment, a suitable dielectric is a UV curable dielectric. Additional suitable dielectric materials are described below and others may be readily identified those of ordinary skill in the art.

Figure 7:
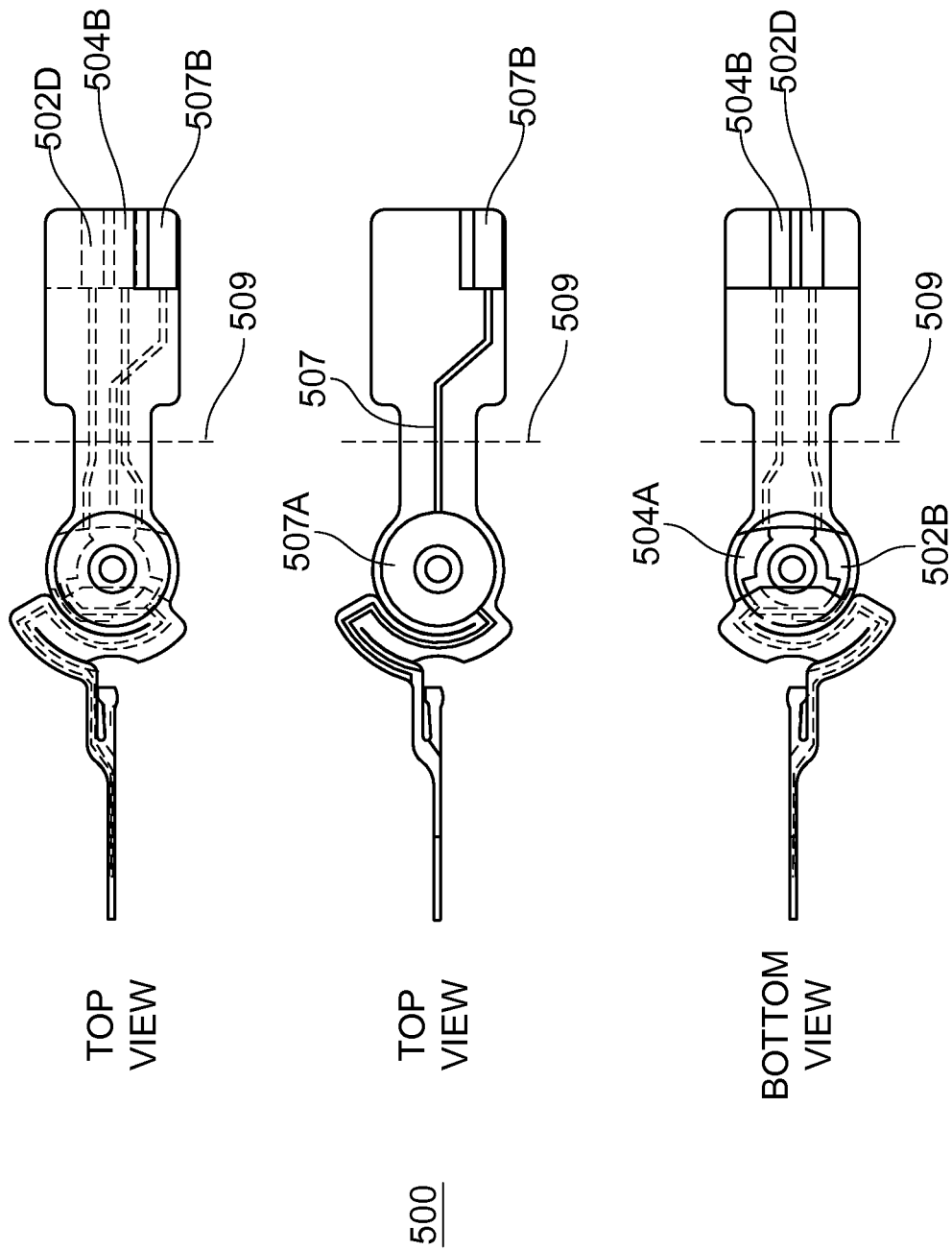
FIG. 7 provides a top transparent view of an analyte sensor assembly according to one embodiment of the present disclosure, a top view of the analyte sensor assembly showing a counter electrode, and a bottom view of the analyte sensor construction showing reference and working electrodes. In some cases, substrate and dielectric layers are shown opaque for clarity.

FIG. 7 provides a top transparent view of the analyte sensor assembly 500 in singulated form; a top view of the analyte sensor assembly 500 in singulated form showing the counter electrode 507; and a bottom view of the analyte sensor assembly 500 in singulated form showing the reference electrode 504 and working electrode 502. Dotted line 509 represents a cut line at which the sensor assembly 500 may be cut to remove excess material prior to or after attachment of the analyte sensor assembly 500 to a sensor control unit. Conductive electrode traces to the right of the cut lines and their corresponding electrical contacts may be used to test the function of the analyte sensor assembly prior to and/or after attachment of the sensor assembly to a sensor control unit. These conductive traces and associated dielectric layers may be removed prior to use of the analyte sensor assembly and an associated sensor control unit, e.g., by cutting along cut line 509. Alternatively, an analyte sensor assembly 500 may be prepared which does not include electrode traces which extend at their proximal end beyond, e.g., the position indicated by cut line 509. In still another embodiment, the various electrode traces are formed to terminate at their proximal ends at electrode contacts 502B, 504A and 507A.

In some embodiments, an analyte sensor according to the present disclosure may include an optional identifier, which uniquely identifies at least one of the analyte sensors, the batch or lot of analyte sensors from which the analyte sensor originated, and/or combinations thereof. The identifier may include, e.g., an alphanumeric identifier, one or more symbols, bar codes, etc. In some embodiments, the identifier provides information identifying the location, e.g., row and column, of the analyte sensor on a sheet containing a plurality of analyte sensors prior to singulation. The identifier may in some embodiments be made from the same conductive material as one or more of the conductive layers of the analyte sensor and may, in some embodiments, be applied or formed in the same manner as one or more of the conductive layers of the analyte sensor, via a printing or ablation method. In some embodiments, the identifier may be provided by removing material from one or more of the insulative layers of the analyte sensor to provide an identifying pattern, e.g., a bar code, and/or an alphanumeric identifier. For example, the identifier may be etched, cut, or ablated into one or more of the insulative layers of the analyte sensor, e.g, the insulative base substrate. In some embodiments, an identifier as described above is used, e.g., during the manufacturing process, to identify a sheet of analyte sensors prior to singulation. In such embodiments, the individual sensors may or may not include an identifier after singulation.

Figure 16A:
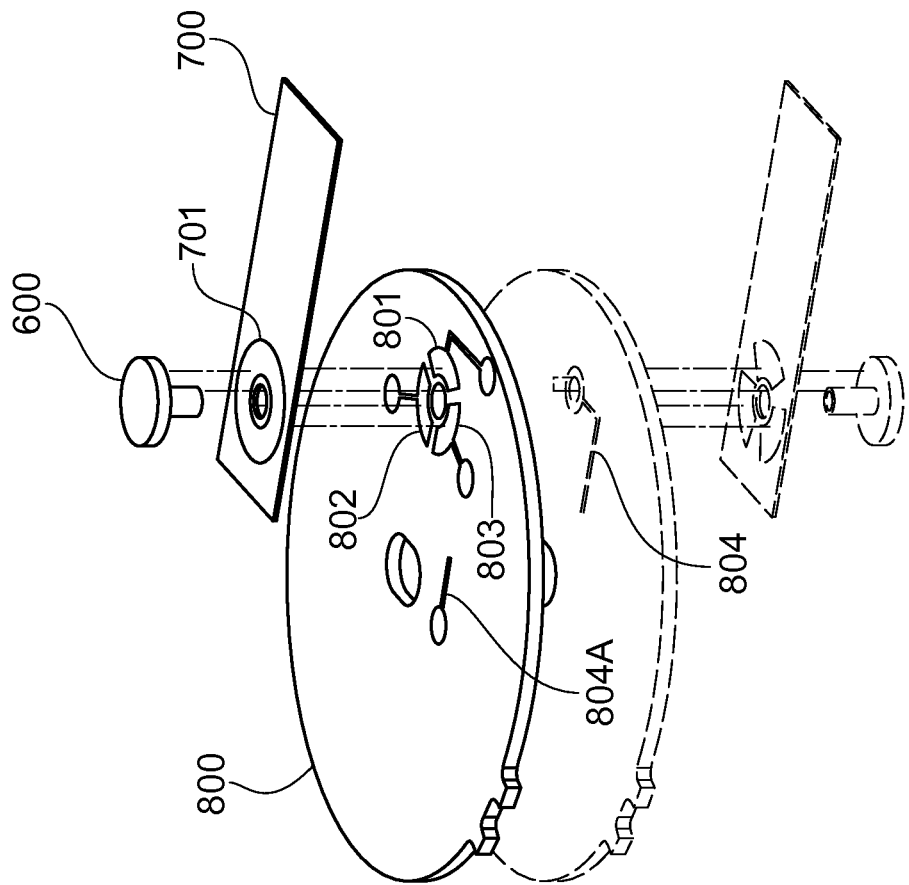
FIGS. 16A and 16B show a generalized sensor connector concept according to one embodiment of the present disclosure. 1) The conductive sensor connector, e.g. a conductive rivet, makes contact with an electrical contact on top of an analyte sensor. 2) The conductive sensor connector mechanically holds contacts together making contact between electrical contacts on the bottom of the analyte sensor and electrical contacts on the top of a printed circuit board (PCB). 3) The conductive connector, e.g. rivet, is formed and makes contact with an electrical contact on the bottom of the PCB thereby providing an electrical connection between the electrical contact on top of the analyte sensor and the electrical contact on the bottom of the PCB. (16A) provides an exploded view and a mirrored exploded view of a sensor attached via a rivet to a PCB. (16B) provides another perspective of the exploded view shown in (A).
Figure 16B:
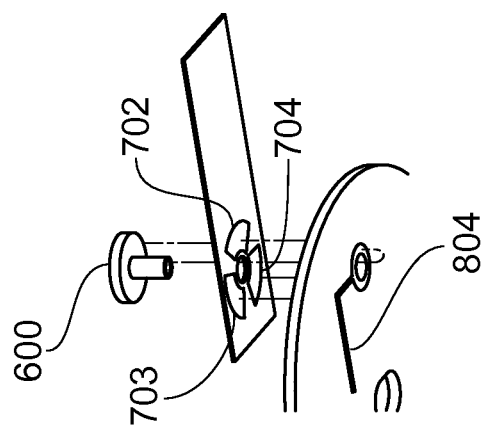

Exemplary embodiments of a double-sided analyte sensor with a sensor connector, e.g., rivet, attachment to a sensor control unit is now described with reference to FIGS. 16A and 16B, which shows a generalized sensor connector concept according to one embodiment of the present disclosure. As shown in FIGS. 16A and 16B, a sensor connector, e.g., a rivet 600, makes contact with an electrical contact 701 (full electrode trace not shown) on a first side, e.g., the top side, of a planar, double-sided analyte sensor 700. The rivet mechanically couples the analyte sensor 700 to a PCB 800 of a sensor control unit thereby providing contact between electrical contacts 702-704 (full electrode traces not shown) on a second side, e.g., the bottom, of the analyte sensor 700 and electrical contacts 801-803 and on a first side, e.g, the top, of the PCB 800. By forming the rivet, e.g., by using a spiral forming, impact forming or orbit forming method, contact between the rivet 600 and a electrical contact 804 on a second side, e.g., the bottom of the PCB 800 is provided which in turn provides an electrical connection between the electrical contact 701 on a first side, e.g., top, of the analyte sensor and the electrical contact 804 on the second side, e.g., bottom, of the PCB 800. In the embodiment shown in FIGS. 16A and 16B, electrical contact 804 includes an electrical trace 804A which extends through PCB 800. In this way, electrical signals to or from each of electrical contacts 702-704 and 701 may be communicated to or from the same side of PCB 800. While FIGS. 16A and 16B indicate an analyte sensor having a four electrode system, one of skill in the art will readily understand that this embodiment may be adjusted to accommodate analyte sensors having any of a variety of electrode configurations. For example, the embodiment of FIGS. 16A and 16B could be adjusted to accommodate a three electrode analyte sensor such as the one described with reference to FIGS. 6-14 above. Similarly, while FIGS. 16A and 16B depict a conductive rivet sensor connector, the embodiment may be adapted to accommodate other conductive connectors as described herein or known in the art.

Stacked Sensor Having First Electrode Narrower than Second Electrode

When manufacturing analyte sensors having at least two electrodes that are stacked, i.e., layered, or sensors which include a stacked electrode configuration, relatively thin insulative layers may be used, e.g., insulative layers having a thickness of about 15 µm to about 150 µm, e.g., about 15 µm to about 100 µm, about 15 µm to about 50 µm, about 15 µm to about 40 µm, about 15 µm to about 30 µm, about 15 µm to about 25 µm, or about 20 µm, to reduce the cross-sectional area of the sensor or a portion thereof. This may be desirable, for example, where the analyte sensor is completely body-implanted or partially body-implanted. By reducing the cross-sectional area of the analyte sensor, an analyte sensor is produced which can be inserted while causing less pain and/or discomfort to the user.

For example, with reference to FIGS. 1A-1D, a sensor 10 is provided which includes insulative layers 13 and 15. Insulative layers 13 and 15 may be thin relative to generally planar insulative base substrate layer 11, or vice versa. For example, insulative layers 13 and 15 may have a thickness in the range of 15-30 µm while substrate layer 11 has a thickness in the range of 0.1 to 0.15 mm. Such sensors may be manufactured in sheets wherein a single sheet includes a plurality of sensors. However, such a process generally requires singulation of the sensors prior to use. Where such singulation requires cutting through two or more conductive layers which are separated by insulative layers, shorting between the two conductive layers may occur, particularly if the insulative layers are thin. In order to avoid such shorting, fewer than all of the conductive layers may be cut through during the singulation process. For example, at least one of the conductive layers may be provided at least in part as an electrode, e.g., including a conductive trace, having a narrow width relative to one or more other conductive layers such that during the singulation process a first conductive layer separated from a second conductive layer only by a thin insulative layer, e.g., an insulative layer having a thickness in the range of 15-30 µm, is cut while a second conductive layer is not.

Figure 1B:
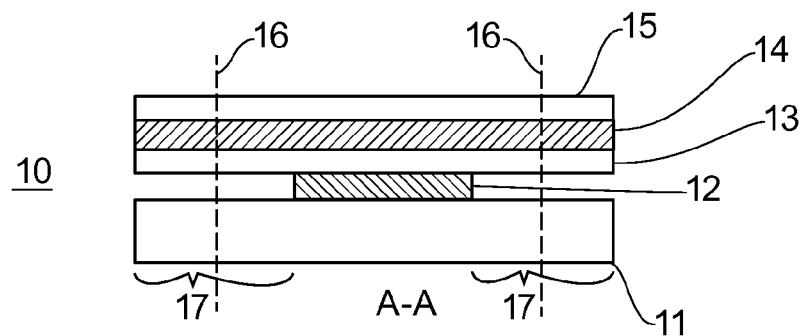
FIG. 1B shows a cross-section of the analyte sensor depicted in FIG. 1A taken along lines A-A.
Figure 1C:
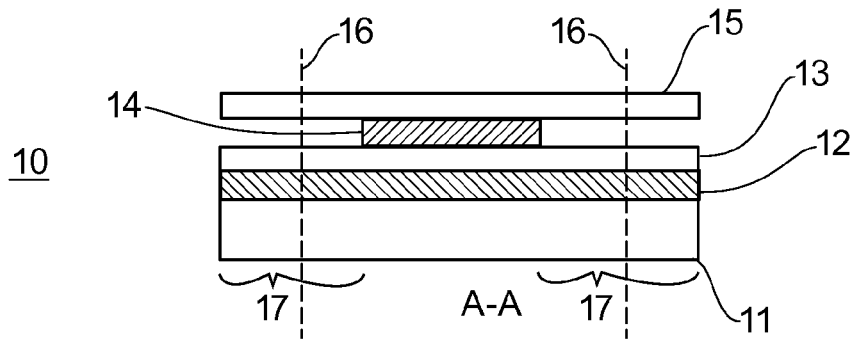
FIG. 1C shows a cross-section of an alternative embodiment of the analyte sensor depicted in FIG. 1A taken along lines A-A.
Figure 1D:
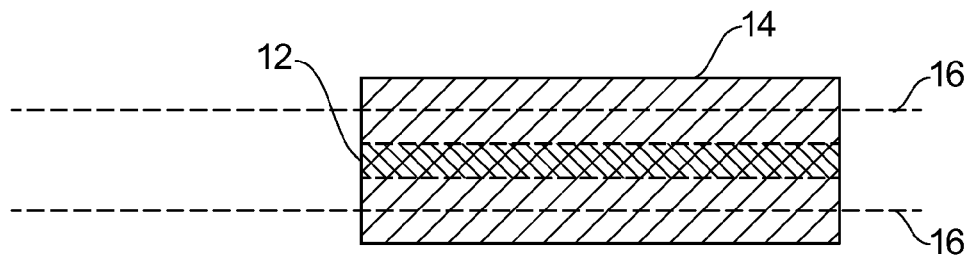
FIG. 1D shows a top view of the analyte sensor depicted in FIGS. 1A and 1B. The insulative layers are not shown so that the two conductive layers are visible.

For example, with reference to FIGS. 1A and 1C, a sensor 10 includes an at least generally planar insulative base substrate 11. Positioned on the at least generally planar insulative base substrate 11 is a first conductive layer 12. A first relatively thin insulative layer 13, e.g., an insulative layer having a thickness in the range of 15-30 µm, is positioned on the first conductive layer 12 and second conductive layer 14 is positioned on the relatively thin insulative layer 13. Finally, a second relatively thin insulative layer 15, e.g., an insulative layer having a thickness in the range of 15-30 µm, is positioned on the second conductive layer 14. As shown in FIG. 1B, first conductive layer 12 may be a an electrode having a narrow width relative to conductive layer 14 as shown in the FIG. 1B cross-section taken at lines A-A. Alternatively, second conductive layer 14 may be a conductive electrode having a narrow width relative to conductive layer 12 as shown in the FIG. 1C cross-section taken at lines A-A. Singulation cut lines 16 are shown in FIGS. 1B, 1C and 1D. The sensor may be singulated, for example, by cutting to either side of the relatively narrow conductive electrode, e.g., in regions 17, as shown in FIGS. 1B, 1C and 1D. With reference to FIGS. 1B and 1D, singulation by cutting along singulation cut lines 16 results in cutting through conductive layer 14 but not conductive layer 12. With reference to FIG. 1C, singulation by cutting along singulation cut lines 16 results in cutting through conductive layer 12 but not conductive layer 14.

FIG. 1D shows an embodiment of the sensor shown in FIG. 1B as it may be provided prior to singulation during the manufacturing process. It should be noted that while FIGS. 1B and 1C appear to depict empty space to either side of conductive layers 12 and 14 respectively, one of ordinary skill in the art will understand that insulative layers 13 and/or 15, may extend into these spaces thereby covering side edges of conductive layer 12 and 14 respectively.

In an embodiment, first conductive layer 12 is an electrode having a relatively narrow width relative to conductive layer 14 and is a working electrode while conductive layer 14 is a reference electrode or counter/reference electrode. In another embodiment, second conductive layer 14 is an electrode having a relatively narrow width relative to conductive layer 12 and is a working electrode while conductive layer 12 is a reference electrode or counter/reference electrode.

In addition, one of the conductive layers may be spaced back from the other conductive layer at the distal end of the sensor, e.g., the sensing end of the sensor. One of the conductive layers may extend, for example, to the distal tip of the sensor while the other terminates proximal to the distal tip of the sensor. In this manner, the sensor may be cut perpendicularly to the length of the sensor and across one of the conductive layers without cutting through two conductive layers separated by only a thin insulative layer e.g., an insulative layer having a thickness in the range of 15-30 µm. In the embodiment depicted in FIG. 1A the second conductive layer 14 is spaced back distally relative to the first conductive layer 12. While FIGS. 1A-1D depict a two electrode sensor, it should be noted that this sensor structure may be readily modified to accommodate additional electrode layers, e.g., in the case of sensors having 3 or 4 electrodes.

Electrochemical Sensors

Embodiments of the present disclosure relate to methods and devices for detecting at least one analyte, including glucose, in body fluid. Embodiments relate to the continuous and/or automatic in vivo monitoring of the level of one or more analytes using a continuous analyte monitoring system that includes an analyte sensor at least a portion of which is to be positioned beneath a skin surface of a user for a period of time and/or the discrete monitoring of one or more analytes using an in vitro blood glucose ("BG") meter and an analyte test strip. Embodiments include combined or combinable devices, systems and methods and/or transferring data between an in vivo continuous system and an in vitro system. In some embodiments, the systems, or at least a portion of the systems, are integrated into a single unit.

A sensor as described herein may be an in vivo sensor or an in vitro sensor (e.g., a discrete monitoring test strip). In certain embodiments, the sensor is a single-sided analyte sensor as described herein. In other embodiments, the sensor is a double-sided analyte sensor as described herein.

Embodiments of the present disclosure include analyte monitoring devices and systems that include an analyte sensor, at least a portion of which is positionable beneath the skin surface of the user for the in vivo detection of an analyte, including glucose, lactate, and the like, in a body fluid. Embodiments include wholly implantable analyte sensors and analyte sensors in which only a portion of the sensor is positioned under the skin and a portion of the sensor resides above the skin, e.g., for contact to an electronics unit, such as a sensor control unit (which may include a transmitter), a receiver/display unit, transceiver, processor, etc. The sensor may be, for example, subcutaneously positionable in a user for the continuous or periodic monitoring of a level of an analyte in the user's interstitial fluid. For the purposes of this description, continuous monitoring and periodic monitoring will be used interchangeably, unless noted otherwise and are intended to include both continuous and on-demand analyte measurement systems known in the art. The sensor response may be correlated and/or converted to analyte levels in blood or other fluids. In certain embodiments, an analyte sensor may be positioned in contact with interstitial fluid to detect the level of glucose, which detected glucose may be used to infer the glucose level in the user's bloodstream. Analyte sensors may be insertable into a vein, artery, or other portion of the body containing fluid. Embodiments of the analyte sensors may be configured for monitoring the level of the analyte over a time period which may range from seconds, minutes, hours, days, weeks, to months, or longer.

In certain embodiments, the analyte sensors, such as glucose sensors, are capable of in vivo detection of an analyte for one hour or more, e.g., a few hours or more, e.g., a few days or more, e.g., three or more days, e.g., five days or more, e.g., seven days or more such as fourteen days or more, e.g., several weeks or more such as 3 weeks or more, or one month or more. Future analyte levels may be predicted based on information obtained, e.g., the current analyte level at time $t_0$, the rate of change of the analyte, etc. Predictive alarms may notify the user of a predicted analyte level that may be of concern in advance of the user's analyte level reaching the future predicted analyte level. This provides the user an opportunity to take corrective action.

Analytes that may be monitored include, but are not limited to, acetyl choline, amylase, bilirubin, cholesterol, chorionic gonadotropin, glycosylated hemoglobin (HbA1c), creatine kinase (e.g., CK-MB), creatine, creatinine, DNA, fructosamine, glucose, glucose derivatives, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times.

Analyte sensors may include an analyte-responsive enzyme to provide a sensing element. Some analytes, such as oxygen, can be directly electrooxidized or electroreduced on a sensor, and more specifically at least on a working electrode of a sensor. Other analytes, such as glucose and lactate, require the presence of at least one electron transfer agent and/or at least one catalyst to facilitate the electrooxidation or electroreduction of the analyte. Catalysts may also be used for those analytes, such as oxygen, that can be directly electrooxidized or electroreduced on the working electrode. For these analytes, each working electrode includes a sensing element proximate to or on a surface of a working electrode. In many embodiments, a sensing element is formed near or on only a small portion of at least a working electrode.

Each sensing element includes one or more components constructed to facilitate the electrochemical oxidation or reduction of the analyte. The sensing element may include, for example, a catalyst to catalyze a reaction of the analyte and produce a response at the working electrode, an electron transfer agent to transfer electrons between the analyte and the working electrode (or other component), or both.

A variety of different sensing element configurations may be used. In certain embodiments, the sensing elements are deposited on the conductive material of a working electrode. The sensing elements may extend beyond the conductive material of the working electrode. In some cases, the sensing elements may also extend over other electrodes, e.g., over the counter electrode and/or reference electrode (or counter/reference where provided). In other embodiments, the sensing elements are contained on the working electrode, such that the sensing elements do not extend beyond the conductive material of the working electrode. In some embodiments a working electrode is configured to include a plurality of spatially distinct sensing elements. Additional information related to the use of spatially distinct sensing elements can be found in U.S. Provisional Application No. 61/421,371, entitled "Analyte Sensors with Reduced Sensitivity Variation," which was filed on Dec. 9, 2010, and which is incorporated by reference herein in its entirety and for all purposes.

The terms "working electrode", "counter electrode", "reference electrode" and "counter/reference electrode" are used herein to refer to conductive sensor components, including, e.g., conductive traces, which are configured to function as a working electrode, counter electrode, reference electrode or a counter/reference electrode respectively. For example, a working electrode includes that portion of a conductive material, e.g., a conductive trace, which functions as a working electrode as described herein, e.g., that portion of a conductive material which is exposed to an environment containing the analyte or anlaytes to be measured, and which, in some cases, has been modified with one or more sensing elements as described herein. Similarly, a reference electrode includes that portion of a conductive material, e.g., conductive trace, which function as a reference electrode as described herein, e.g., that portion of a conductive material which is exposed to an environment containing the analyte or anlaytes to be measured, and which, in some cases, includes a secondary conductive layer, e.g., a Ag/AgCl layer. A counter electrode includes that portion of a conductive material, e.g., conductive trace which is configured to function as a counter electrode as described herein, e.g., that portion of a conductive trace which is exposed to an environment containing the analyte or anlaytes to be measured. As noted above, in some embodiments, a portion of a conductive material, e.g., conductive trace, may function as either or both of a counter electrode and a reference electrode. In addition, "working electrodes", "counter electrodes", "reference electrodes" and "counter/reference electrodes" may include portions, e.g., conductive traces, electrical contacts, or areas or portions thereof, which do not include sensing elements but which are used to electrically connect the electrodes to other electrical components.

Sensing elements that are in direct contact with the working electrode, e.g, the working electrode trace, may contain an electron transfer agent to transfer electrons directly or indirectly between the analyte and the working electrode, and/or a catalyst to facilitate a reaction of the analyte. For example, a glucose, lactate, or oxygen electrode may be formed having sensing elements which contain a catalyst, including glucose oxidase, glucose dehydrogenase, lactate oxidase, or laccase, respectively, and an electron transfer agent that facilitates the electrooxidation of the glucose, lactate, or oxygen, respectively.

In other embodiments the sensing elements are not deposited directly on the working electrode, e.g, the working electrode trace. Instead, the sensing elements may be spaced apart from the working electrode trace, and separated from the working electrode trace, e.g., by a separation layer. A separation layer may include one or more membranes or films or a physical distance. In addition to separating the working electrode trace from the sensing elements, the separation layer may also act as a mass transport limiting layer and/or an interferent eliminating layer and/or a biocompatible layer.

In certain embodiments which include more than one working electrode, one or more of the working electrodes may not have corresponding sensing elements, or may have sensing elements that do not contain one or more components (e.g., an electron transfer agent and/or catalyst) needed to electrolyze the analyte. Thus, the signal at this working electrode may correspond to background signal which may be removed from the analyte signal obtained from one or more other working electrodes that are associated with fully-functional sensing elements by, for example, subtracting the signal.

In certain embodiments, the sensing elements include one or more electron transfer agents. Electron transfer agents that may be employed are electroreducible and electrooxidizable ions or molecules having redox potentials that are a few hundred millivolts above or below the redox potential of the standard calomel electrode (SCE). The electron transfer agent may be organic, organometallic, or inorganic. Examples of organic redox species are quinones and species that in their oxidized state have quinoid structures, such as Nile blue and indophenol. Examples of organometallic redox species are metallocenes including ferrocene. Examples of inorganic redox species are hexacyanoferrate (III), ruthenium hexamine, etc. Additional examples include those described in U.S. Pat. Nos. 6,736,957, 7,501,053 and 7,754,093, the disclosures of each of which are incorporated herein by reference in their entirety.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic, organometallic or inorganic redox species may be bound to a polymer and used as an electron transfer agent, in certain embodiments the redox species is a transition metal compound or complex, e.g., osmium, ruthenium, iron, and cobalt compounds or complexes. It will be recognized that many redox species described for use with a polymeric component may also be used, without a polymeric component.

Embodiments of polymeric electron transfer agents may contain a redox species covalently bound in a polymeric composition. An example of this type of mediator is poly (vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation. Another example of an ionically-bound mediator is a positively charged polymer including quaternized poly(4-vinyl pyridine) or poly(1-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2, 2'-bipyridines, including 4,4'-dimethoxy-2,2'-bipyridine. Derivatives of 1,10-phenanthroline for complexation with the osmium cation include but are not limited to 4,7-dimethyl-1, 10-phenanthroline and mono-, di-, and polyalkoxy-1,10-phenanthrolines, such as 4,7-dimethoxy-1,10-phenanthroline. Polymers for complexation with the osmium cation include but are not limited to polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole, e.g., electron transfer agents with osmium complexed to a polymer or copolymer of poly(1-vinyl imidazole).

Embodiments may employ electron transfer agents having a redox potential ranging from about −200 mV to about +200 mV versus the standard calomel electrode (SCE). The sensing elements may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, including a glucose oxidase, glucose dehydrogenase (e.g., pyrroloquinoline quinone (PQQ), dependent glucose dehydrogenase, flavine adenine dinucleotide (FAD) dependent glucose dehydrogenase, or nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, a catalyst may be attached to a polymer, cross linking the catalyst with another electron transfer agent, which, as described above, may be polymeric. A second catalyst may also be used in certain embodiments. This second catalyst may be used to catalyze a reaction of a product compound resulting from the catalyzed reaction of the analyte. The second catalyst may operate with an electron transfer agent to electrolyze the product compound to generate a signal at the working electrode. Alternatively, a second catalyst may be provided in an interferent-eliminating layer to catalyze reactions that remove interferents.

In certain embodiments, the sensor works at a low oxidizing potential, e.g., a potential of about +40 mV vs. Ag/AgCl. This sensing elements use, for example, an osmium (Os)-based mediator constructed for low potential operation. Accordingly, in certain embodiments the sensing elements are redox active components that include: (1) osmium-based mediator molecules that include (bidente) ligands, and (2) glucose oxidase enzyme molecules. These two constituents are combined together in the sensing elements of the sensor.

A mass transport limiting layer (not shown), e.g., an analyte flux modulating layer, may be included with the sensor to act as a diffusion-limiting barrier to reduce the rate of mass transport of the analyte, for example, glucose or lactate, into the region around the working electrodes. The mass transport limiting layers are useful in limiting the flux of an analyte to a working electrode in an electrochemical sensor so that the sensor is linearly responsive over a large range of analyte concentrations and is easily calibrated. Mass transport limiting layers may include polymers and may be biocompatible. A mass transport limiting layer may provide many functions, e.g., biocompatibility and/or interferent-eliminating functions, etc.

A mass transport limiting layer may be applied to an analyte sensor as described herein via any of a variety of suitable methods, including, e.g., dip coating and slot die coating.

In certain embodiments, a mass transport limiting layer is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like.

A membrane may be formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to "fine-tune" the permeability of the resulting membrane to an analyte of interest. Optional hydrophilic modifiers, such as poly (ethylene glycol), hydroxyl or polyhydroxyl modifiers, may be used to enhance the biocompatibility of the polymer or the resulting membrane.

A membrane may be formed in situ by applying an alcohol-buffer solution of a crosslinker and a modified polymer over the enzyme-containing sensing elements and allowing the solution to cure for about one to two days or other appropriate time period. The crosslinker-polymer solution may be applied over the sensing elements by placing a droplet or droplets of the membrane solution on the sensor, by dipping the sensor into the membrane solution, by spraying the membrane solution on the sensor, and the like. Generally, the thickness of the membrane is controlled by the concentration of the membrane solution, by the number of droplets of the membrane solution applied, by the number of times the sensor is dipped in the membrane solution, by the volume of membrane solution sprayed on the sensor, or by any combination of these factors. In order to coat the distal and side edges of the sensor, the membrane material may have to be applied subsequent to singulation of the sensor precursors. In some embodiments, the analyte sensor is dip-coated following singulation to apply one or more membranes. Alternatively, the analyte sensor could be slot-die coated wherein each side of the analyte sensor is coated separately. A membrane applied in the above manner may have any combination of the following functions: (1) mass transport limitation, i.e., reduction of the flux of analyte that can reach the sensing elements, (2) biocompatibility enhancement, or (3) interferent reduction.

In some embodiments, a membrane composition for use as a mass transport limiting layer may include one or more leveling agents, e.g., polydimethylsiloxane (PDMS). Additional information with respect to the use of leveling agents can be found, for example, in US Patent Application Publication No. US 2010/0081905, the disclosure of which is incorporated by reference herein in its entirety.

In some instances, the membrane may form one or more bonds with the sensing elements. By bonds is meant any type of an interaction between atoms or molecules that allows chemical compounds to form associations with each other, such as, but not limited to, covalent bonds, ionic bonds, dipole-dipole interactions, hydrogen bonds, London dispersion forces, and the like. For example, in situ polymerization of the membrane can form crosslinks between the polymers of the membrane and the polymers in the sensing elements. In certain embodiments, crosslinking of the membrane to the sensing element facilitates a reduction in the occurrence of delamination of the membrane from the sensor.

In certain embodiments, the sensing system detects hydrogen peroxide to infer glucose levels. For example, a hydrogen peroxide-detecting sensor may be constructed in which the sensing elements include an enzyme such as glucose oxidase, glucose dehydrogenase, or the like, and is positioned on the working electrode. The sensing elements may be covered by one or more layers, e.g., a membrane that is selectively permeable to glucose. Once the glucose passes through the membrane, it is oxidized by the enzyme and reduced glucose oxidase can then be oxidized by reacting with molecular oxygen to produce hydrogen peroxide.

Certain embodiments include a hydrogen peroxide-detecting sensor constructed from sensing elements prepared by combining together, for example: (1) a redox mediator having a transition metal complex including an Os polypyridyl complex with oxidation potentials of about +200 mV vs. SCE, and (2) periodate oxidized horseradish peroxidase (HRP). Such a sensor functions in a reductive mode; the working electrode is controlled at a potential negative to that of the Os complex, resulting in mediated reduction of hydrogen peroxide through the HRP catalyst.

In another example, a potentiometric sensor can be constructed as follows. Glucose-sensing elements may be constructed by combining together (1) a redox mediator having a transition metal complex including Os polypyridyl complexes with oxidation potentials from about −200 mV to +200 mV vs. SCE, and (2) glucose oxidase. This sensor can then be used in a potentiometric mode, by exposing the sensor to a glucose containing solution, under conditions of zero current flow, and allowing the ratio of reduced/oxidized Os to reach an equilibrium value. The reduced/oxidized Os ratio varies in a reproducible way with the glucose concentration, and will cause the electrode's potential to vary in a similar way.

The substrate may be formed using a variety of non-conducting materials, including, for example, polymeric or plastic materials and ceramic materials. Suitable materials for a particular sensor may be determined, at least in part, based on the desired use of the sensor and properties of the materials.

In some embodiments, the substrate is flexible. For example, if the sensor is configured for implantation into a user, then the sensor may be made flexible (although rigid sensors may also be used for implantable sensors) to reduce pain to the user and damage to the tissue caused by the implantation of and/or the wearing of the sensor. A flexible substrate often increases the user's comfort and allows a wider range of activities. Suitable materials for a flexible substrate include, for example, non-conducting plastic or polymeric materials and other non-conducting, flexible, deformable materials. Examples of useful plastic or polymeric materials include thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate).

In other embodiments, the sensors are made using a relatively rigid substrate to, for example, provide structural support against bending or breaking. Examples of rigid materials that may be used as the substrate include poorly conducting ceramics, such as aluminum oxide and silicon dioxide. An implantable sensor having a rigid substrate may have a sharp point and/or a sharp edge to aid in implantation of a sensor without an additional insertion device.

It will be appreciated that for many sensors and sensor applications, both rigid and flexible sensors will operate adequately. The flexibility of the sensor may also be controlled and varied along a continuum by changing, for example, the composition and/or thickness of the substrate.

In addition to considerations regarding flexibility, it is often desirable that implantable sensors should have a substrate which is physiologically harmless, for example, a substrate approved by a regulatory agency or private institution for in vivo use.

The sensor may include optional features to facilitate insertion of an implantable sensor. For example, the sensor may be pointed at the tip to ease insertion. In addition, the sensor may include a barb which assists in anchoring the sensor within the tissue of the user during operation of the sensor. However, the barb is typically small enough so that little damage is caused to the subcutaneous tissue when the sensor is removed for replacement.

An implantable sensor may also, optionally, have an anticlotting agent disposed on a portion of the substrate which is implanted into a user. This anticlotting agent may reduce or eliminate the clotting of blood or other body fluid around the sensor, particularly after insertion of the sensor. Blood clots may foul the sensor or irreproducibly reduce the amount of analyte which diffuses into the sensor. Examples of useful anticlotting agents include heparin and tissue plasminogen activator (TPA), as well as other known anticlotting agents.

The anticlotting agent may be applied to at least a portion of that part of the sensor that is to be implanted. The anticlotting agent may be applied, for example, by bath, spraying, brushing, or dipping, etc. The anticlotting agent is allowed to dry on the sensor. The anticlotting agent may be immobilized on the surface of the sensor or it may be allowed to diffuse away from the sensor surface. The quantities of anticlotting agent disposed on the sensor may be below the amounts typically used for treatment of medical conditions involving blood clots and, therefore, have only a limited, localized effect.

Figure 17:
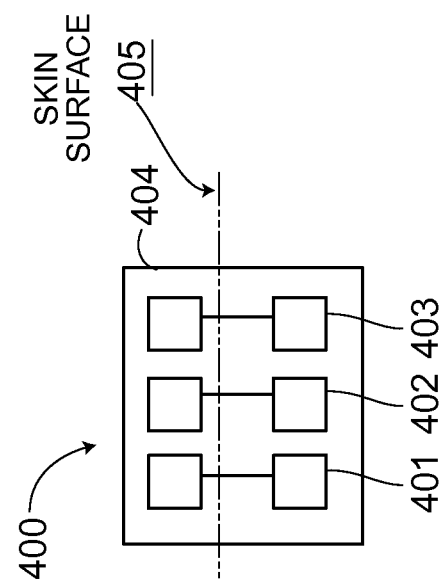
FIG. 17 shows a schematic diagram of an embodiment of an analyte sensor according to some embodiments of the present disclosure.

FIG. 17 schematically shows an analyte sensor 400 in accordance with one embodiment of the present disclosure. This sensor embodiment includes electrodes 401, 402 and 403 on a base 404. Electrodes (and/or other features) may be applied or otherwise processed using any suitable technology, e.g., chemical vapor deposition (CVD), physical vapor deposition, sputtering, reactive sputtering, printing, coating, ablating (e.g., laser ablation), painting, dip coating, etching, and the like. Materials include, but are not limited to, any one or more of aluminum, carbon (including graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., doped polycrystalline silicon), silver, tantalum, tin, titanium, tungsten, uranium, vanadium, zinc, zirconium, mixtures thereof, and alloys, oxides, or metallic compounds of these elements.

The analyte sensor 400 may be wholly implantable in a user or may be configured so that only a portion is positioned within (internal) a user and another portion outside (external) a user. For example, the sensor 400 may include a first portion positionable above a surface of the skin 405, and a second portion positioned below the surface of the skin. In such embodiments, the external portion may include contacts (connected to respective electrodes of the second portion by traces) to connect to another device also external to the user such as a transmitter unit. While the embodiment of FIG. 17 shows three electrodes side-by-side on the same surface of base 404, other configurations are contemplated, e.g., fewer or greater electrodes, some or all electrodes on different surfaces of the base or present on another base, some or all electrodes stacked together, electrodes of differing materials and dimensions, etc. Additional sensor configurations are discussed herein.

Data Monitoring and Management Systems

Figure 18:
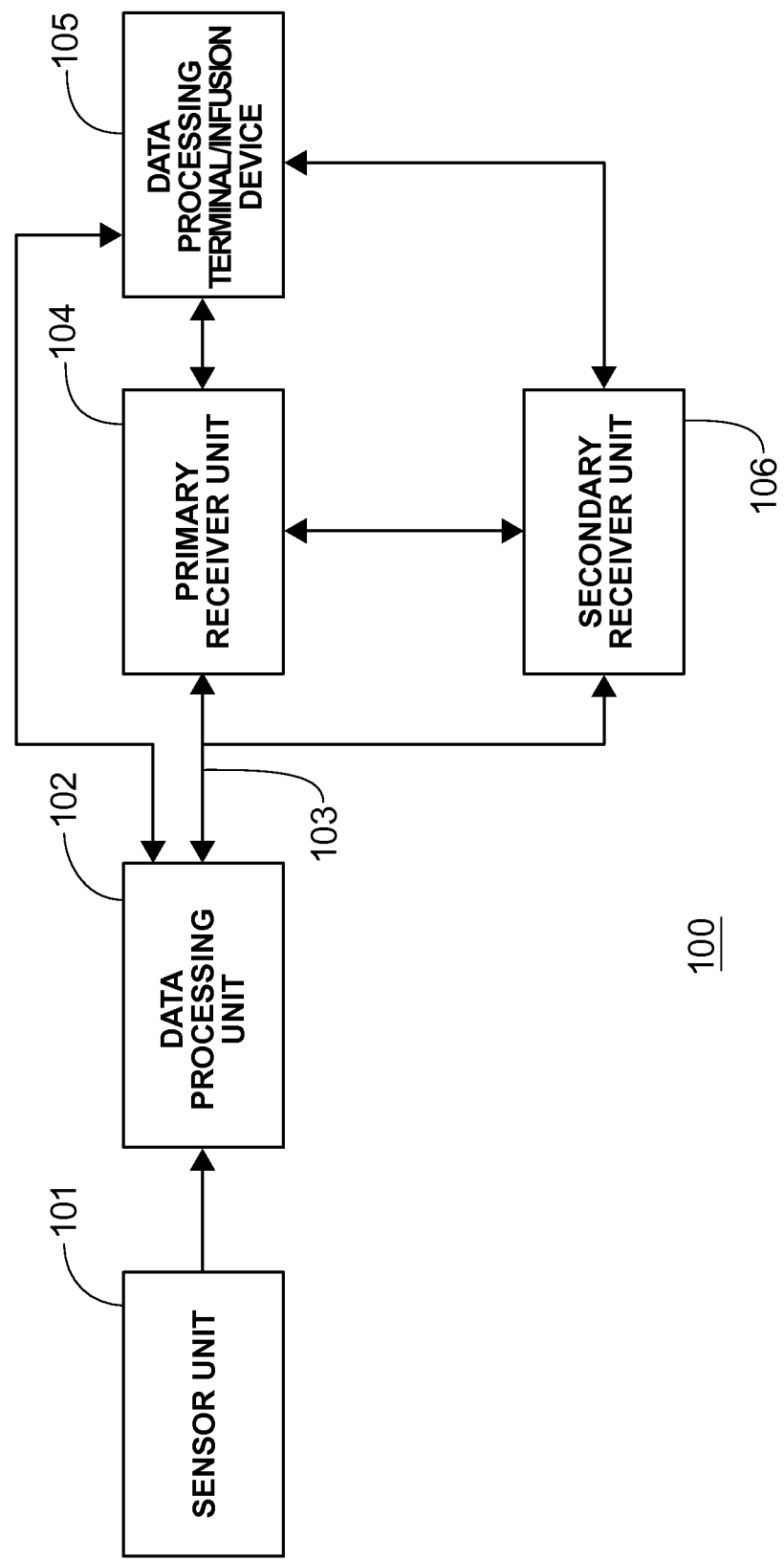
FIG. 18 shows a block diagram of an embodiment of an analyte monitoring system according to embodiments of the present disclosure.

The analyte sensors and associated devices described herein may be used in the context of one or more data monitoring and management systems. FIG. 18 shows a data monitoring and management system such as, for example, an analyte (e.g., glucose) monitoring system 100 in accordance with certain embodiments. Aspects of the subject disclosure are further described primarily with respect to glucose monitoring devices and systems, and methods of glucose detection, for convenience only and such description is in no way intended to limit the scope of the embodiments. It is to be understood that the analyte monitoring system may be configured to monitor a variety of analytes at the same time or at different times.

The analyte monitoring system 100 includes an analyte sensor 101 (e.g., a single-sided or double-sided analyte sensor as described herein), a data processing unit 102 connectable to the sensor 101, and a primary receiver unit 104. The terms "sensor control unit" and "data processing unit" are used interchangeably herein. In some instances, the primary receiver unit 104 is configured to communicate with the data processing unit 102 via a communication link 103. In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link 107, which may optionally be configured for bi-directional communication. Further, the data processing unit 102 may include a transmitter or a transceiver to transmit and/or receive data to and/or from the primary receiver unit 104 and/or the data processing terminal 105 and/or optionally a secondary receiver unit 106.

Referring again to FIG. 18, the primary receiver unit 104 may include an in vitro analyte meter, a personal computer, a portable computer including a laptop or a handheld device (e.g., a personal digital assistant (PDA), a tablet computer, a telephone including a mobile phone (e.g., a multimedia and Internet-enabled mobile phone including an iPhone™, a Blackberry®, or similar phone), a digital player (e.g., an iPOD™, etc.), a pager, and the like), a drug delivery device (e.g., an infusion device), or devices including combinations thereof, each of which may be configured for data communication with the data processing unit 102 via a wired or a wireless connection. Additionally, the primary receiver unit 104 may further be connected to a data network (not shown) for storing, retrieving, updating, and/or analyzing data corresponding to the detected analyte level of the user.

Also shown in FIG. 18 is an optional secondary receiver unit 106 which is operatively coupled to the communication link 103 and configured to receive data transmitted from the data processing unit 102. The secondary receiver unit 106 may be configured to communicate with the primary receiver unit 104, as well as the data processing terminal 105. In certain embodiments, the secondary receiver unit 106 may be configured for bi-directional wireless communication with each of the primary receiver unit 104 and the data processing terminal 105. As discussed in further detail below, in some instances, the secondary receiver unit 106 may be a de-featured receiver as compared to the primary receiver unit 104, for instance, the secondary receiver unit 106 may include a limited or minimal number of functions and features as compared with the primary receiver unit 104. As such, the secondary receiver unit 106 may include a smaller (in one or more, including all, dimensions), compact housing or embodied in a device including a wrist watch, arm band, PDA, mp3 player, mobile phone, etc., for example. Alternatively, the secondary receiver unit 106 may be configured with the same or substantially similar functions and features as the primary receiver unit 104. The secondary receiver unit 106 may include a docking portion configured to mate with a docking cradle unit for placement by, e.g., the bedside for night time monitoring, and/or a bi-directional communication device. A docking cradle may recharge a power supply.

Only one analyte sensor 101, data processing unit 102 and data processing terminal 105 are shown in the embodiment of the analyte monitoring system 100 illustrated in FIG. 18. However, it will be appreciated by one of ordinary skill in the art that the analyte monitoring system 100 may include more than one sensor 101 and/or more than one data processing unit 102, and/or more than one data processing terminal 105. Multiple sensors may be positioned in a user for analyte monitoring at the same or different times. In certain embodiments, analyte information obtained by a first sensor positioned in a user may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the sensor 101 is physically positioned in or on the body of a user whose analyte level is being monitored. The sensor 101 may be configured to at least periodically sample the analyte level of the user and convert the sampled analyte level into a corresponding signal for transmission by the data processing unit 102. The data processing unit 102 is coupleable to the sensor 101 so that both devices are positioned in or on the user's body, with at least a portion of the analyte sensor 101 positioned transcutaneously in some embodiments. The data processing unit 102 may include a fixation element, such as an adhesive or the like, to secure it to the user's body. A mount (not shown) attachable to the user and mateable with the data processing unit 102 may be used. For example, a mount may include an adhesive surface. The data processing unit 102 performs data processing functions, where such functions may include, but are not limited to, filtering and encoding of data signals, each of which corresponds to a sampled analyte level of the user, for transmission to the primary receiver unit 104 via the communication link 103. In some embodiments, the sensor 101 or the data processing unit 102 or a combined sensor/data processing unit may be wholly implantable under the skin surface of the user.

In certain embodiments, the primary receiver unit 104 may include an analog interface section including an RF receiver and an antenna that is configured to communicate with the data processing unit 102 via the communication link 103, and a data processing section for processing the received data from the data processing unit 102 including data decoding, error detection and correction, data clock generation, data bit recovery, etc., or any combination thereof.

In operation, the primary receiver unit 104 in certain embodiments is configured to synchronize with the data processing unit 102 to uniquely identify the data processing unit 102, based on, for example, an identification information of the data processing unit 102, and thereafter, to periodically receive signals transmitted from the data processing unit 102 associated with the monitored analyte levels detected by the sensor 101.

Referring again to FIG. 18, the data processing terminal 105 may include a personal computer, a portable computer including a laptop or a handheld device (e.g., a personal digital assistant (PDA), a tablet computer, a telephone including a mobile phone (e.g., a multimedia and Internet-enabled mobile phone including an iPhone™, a Blackberry®, or similar phone), a digital player (e.g., an iPOD™, etc.), a pager, and the like), and/or a drug delivery device (e.g., an infusion device), each of which may be configured for data communication with the receiver via a wired or a wireless connection. Additionally, the data processing terminal 105 may further be connected to a data network (not shown) for storing, retrieving, updating, and/or analyzing data corresponding to the detected analyte level of the user.

The data processing terminal 105 may include a drug delivery device (e.g., an infusion device), such as an insulin infusion pump or the like, which may be configured to administer a drug (e.g., insulin) to the user, and which may be configured to communicate with the primary receiver unit 104 for receiving, among others, the measured analyte level. Alternatively, the primary receiver unit 104 may be configured to integrate an infusion device therein so that the primary receiver unit 104 is configured to administer an appropriate drug (e.g., insulin) to users, for example, for administering and modifying basal profiles, as well as for determining appropriate boluses for administration based on, among others, the detected analyte levels received from the data processing unit 102. An infusion device may be an external device or an internal device, such as a device wholly implantable in a user.

In certain embodiments, the data processing terminal 105, which may include an infusion device, e.g., an insulin pump, may be configured to receive the analyte signals from the data processing unit 102, and thus, incorporate the functions of the primary receiver unit 104 including data processing for managing the user's insulin therapy and analyte monitoring. In certain embodiments, the communication link 103, as well as one or more of the other communication interfaces shown in FIG. 18, may use one or more wireless communication protocols, such as, but not limited to: an RF communication protocol, an infrared communication protocol, a Bluetooth enabled communication protocol, an 802.11x wireless communication protocol, or an equivalent wireless communication protocol which would allow secure, wireless communication of several units (for example, per Health Insurance Portability and Accountability Act (HIPPA) requirements), while avoiding potential data collision and interference.

Figure 19:
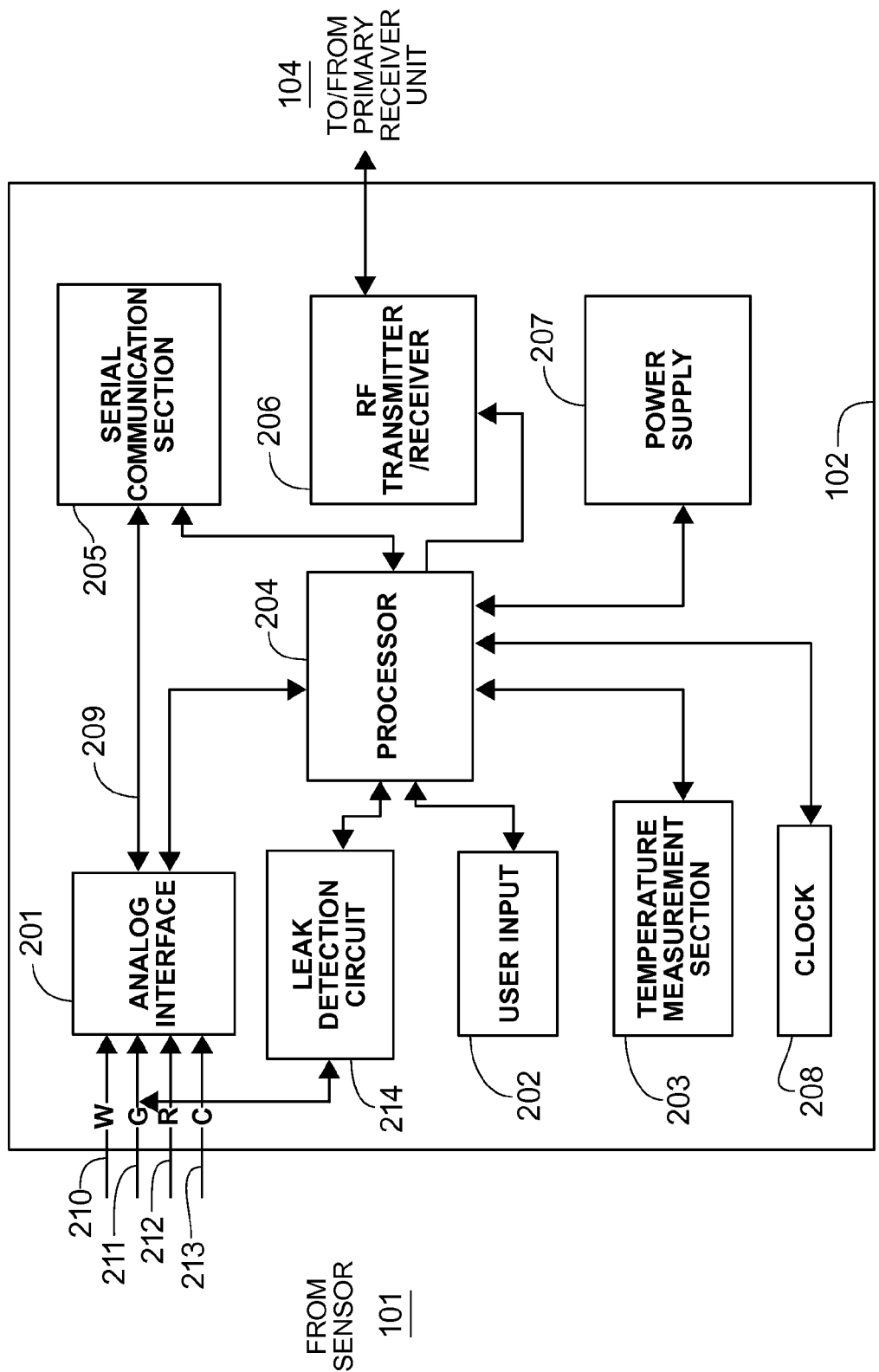
FIG. 19 shows a block diagram of an embodiment of a data processing unit of the analyte monitoring system shown in FIG. 18.

FIG. 19 shows a block diagram of an embodiment of a data processing unit 102 of the analyte monitoring system shown in FIG. 18. User input and/or interface components may be included or a data processing unit may be free of user input and/or interface components. In certain embodiments, one or more application-specific integrated circuits (ASIC) may be used to implement one or more functions or routines associated with the operations of the data processing unit (and/or receiver unit) using for example one or more state machines and buffers.

The data processing unit 102 may include one or more of: an analog interface 201, a user input 202, a temperature measurement section 203, a serial communication section 205, an RF transmitter/receiver 206, a power supply 207, and a clock 208, each of which is operatively coupled to a processor 204.

As can be seen in the embodiment of FIG. 19, the analyte sensor 101 (FIG. 18) may, in some embodiments, include four contacts, three of which are electrodes: a work electrode (W) 210, a reference electrode (R) 212, and a counter electrode (C) 213, each operatively coupled to the analog interface 201 of the data processing unit 102. This embodiment also shows an optional guard contact (G) 211. Fewer or greater electrodes may be employed. For example, the counter and reference electrode functions may be served by a single counter/reference electrode. In some cases, there may be more than one working electrode and/or reference electrode and/or counter electrode, etc.

Figure 20:
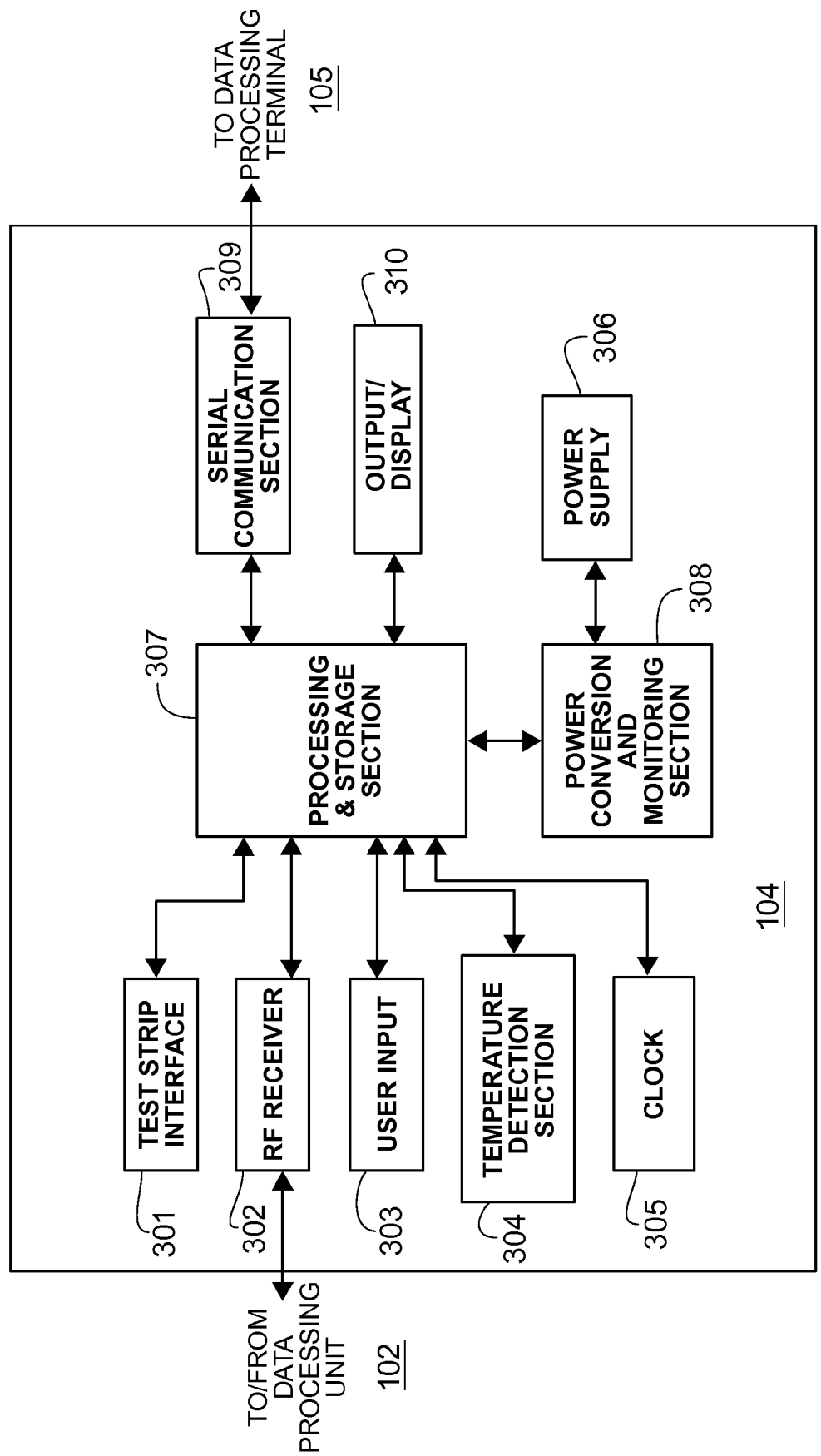
FIG. 20 shows a block diagram of an embodiment of the primary receiver unit of the analyte monitoring system of FIG. 18.

FIG. 20 is a block diagram of an embodiment of a receiver/monitor unit such as the primary receiver unit 104 of the analyte monitoring system shown in FIG. 18. The primary receiver unit 104 may include, for example, one or more of: a test strip interface 301, an RF receiver 302, a user input 303, an optional temperature detection section 304, and a clock 305, each of which is operatively coupled to a processing and storage section 307. The primary receiver unit 104 also includes a power supply 306 operatively coupled to a power conversion and monitoring section 308. Further, the power conversion and monitoring section 308 is also coupled to the processing and storage section 307. Moreover, also shown are a receiver serial communication section 309, and an output/display 310, each operatively coupled to the processing and storage section 307. The primary receiver unit 104 may include user input and/or interface components or may be free of user input and/or interface components.

In certain embodiments, the test strip interface 301 includes an analyte testing portion (e.g., a glucose level testing portion) to receive a blood (or other body fluid sample) analyte test or information related thereto. For example, the test strip interface 301 may include a test strip port to receive a test strip (e.g., a glucose test strip). The device may determine the analyte level of the test strip, and optionally display (or otherwise notice) the analyte level on the output/display 310 of the primary receiver unit 104. Any suitable test strip may be employed, e.g., test strips that only require a very small amount (e.g., 3 microliters or less, e.g., 1 microliter or less, e.g., 0.5 microliters or less, e.g., 0.1 microliters or less), of applied sample to the strip in order to obtain accurate glucose information. Additional test strips that may be utilized include test strips configured to measure more than one analyte, e.g., dual analyte test strips. Embodiments of test strips include, e.g., FreeStyle® blood glucose test strips from Abbott Diabetes Care Inc. (Alameda, Calif.) and Precision™, e.g., Precision Xtra™, test strips from Abbott Diabetes Care Inc. (Alameda, Calif.). Glucose information obtained by an in vitro glucose testing device may be used for a variety of purposes, computations, etc. For example, the information may be used to calibrate sensor 101, confirm results of sensor 101 to increase the confidence thereof (e.g., in instances in which information obtained by sensor 101 is employed in therapy related decisions), etc.

In further embodiments, the data processing unit 102 and/or the primary receiver unit 104 and/or the secondary receiver unit 106, and/or the data processing terminal/infusion device 105 may be configured to receive the analyte value wirelessly over a communication link from, for example, a blood glucose meter. In further embodiments, a user manipulating or using the analyte monitoring system 100 (FIG. 18) may manually input the analyte value using, for example, a user interface (for example, a keyboard, keypad, touch-screen, voice commands, and the like) incorporated in one or more of the data processing unit 102, the primary receiver unit 104, secondary receiver unit 106, or the data processing terminal/infusion device 105.

Additional detailed descriptions are provided in U.S. Pat. Nos. 5,262,035; 5,264,104; 5,262,305; 5,320,715; 5,593,852; 6,175,752; 6,650,471; 6,746, 582, and 7,811,231, each of which is incorporated herein by reference in their entirety.

Sensor Electronics Unit

In some embodiments, a sensor electronics unit, such as a sensor control unit, can be integrated in the sensor, part or all of which is subcutaneously implanted or it can be configured to be placed on the skin of a user. The sensor electronics unit is optionally formed in a shape that is comfortable to the user and which may permit concealment, for example, under a user's clothing. The thigh, leg, upper arm, shoulder, or abdomen are convenient parts of the user's body for placement of the sensor electronics unit to maintain concealment. However, the sensor electronics unit may be positioned on other portions of the user's body. One embodiment of the sensor electronics unit has a thin, oval shape to enhance concealment. However, other shapes and sizes may be used.

The particular profile, as well as the height, width, length, weight, and volume of the sensor electronics unit may vary and depends, at least in part, on the components and associated functions included in the sensor electronics unit. In general, the sensor electronics unit includes a housing typically formed as a single integral unit that rests on the skin of the user. The housing typically contains most or all of the electronic components, e.g., the PCB, of the sensor electronics unit.

The housing of sensor electronics unit may be formed using a variety of materials, including, for example, plastic and polymeric materials, such as rigid thermoplastics and engineering thermoplastics. Suitable materials include, for example, polyvinyl chloride, polyethylene, polypropylene, polystyrene, ABS polymers, and copolymers thereof. The housing of the sensor electronics unit may be formed using a variety of techniques including, for example, injection molding, compression molding, casting, and other molding methods. Hollow or recessed regions may be formed in the housing of the sensor control unit. The electronic components of the sensor electronics unit and/or other items, including a battery or a speaker for an audible alarm, may be placed in the hollow or recessed areas. In some embodiments, the housing of the sensor electronics unit is provided as an overmold structure.

The sensor electronics unit is typically attached to the skin of the user, for example, by adhering the sensor control unit directly to the skin of the user with an adhesive provided on at least a portion of the housing of the sensor control unit which contacts the skin or by suturing the sensor electronics unit to the skin through suture openings in the sensor control unit.

When positioned on the skin of a user, the sensor and the electronic components within a sensor electronics unit, such as a sensor control unit, may be coupled via conductive contacts. For example, one or more working electrodes, counter electrodes (or counter/reference electrodes), reference electrodes, and temperature probes may be attached to individual conductive contacts. For example, the conductive contacts are provided on the interior of the sensor electronics unit. Other embodiments of the sensor control unit have the conductive contacts disposed on the exterior of the housing. The placement of the conductive contacts may be such that they are in contact with the electrical contacts on the sensor when the sensor is properly positioned within the sensor electronics unit.

As discussed previously herein, one or more sensor connectors, e.g., conductive rivets, non-conductive rivets, or partially conductive rivets, may be used to couple the sensor and the electronic components within a sensor electronics unit, such as a sensor control unit. In addition, one or more sensor connectors, e.g., conductive rivets, may be used to connect an electrode, e.g, a conductive trace of the electrode, from one side of an analyte sensor to the other for coupling with the electronic components within the sensor electronics unit.

Embodiments of a sensor electronics unit, such as a sensor control unit, according to the present disclosure and its assembly are now described in more detail with reference to FIGS. 21A-26E which depict various aspects of a sensor control unit insertion assembly 900. FIGS. 21A-22 depict a sensor control unit insertion assembly 900, including a skin patch 904, an overmold structure 905 and a sensor insertion device 901, which in turn includes an insertion needle 902 and a needle hub assembly 903. Skin patch 904 is configured for attachment to the skin of a patient and/or user and includes an adhesive bottom 904B to facilitate such attachment. Skin patch 904 also includes an adhesive top 904A for attachment of the skin patch 904 to the overmold structure 905, a needle opening 904D, through which needle 902 may extend, and a thermistor opening 904C, through which a thermistor 909 may be exposed. See, e.g., FIGS. 22 and 26A-26E. The overmold structure 905 may be made from a variety of suitable materials, e.g., a suitable thermoplastic material (e.g., a moldable polyimide). In one embodiment, overmold structure 905 is made from a suitable resin material. The sensor control unit insertion assembly 900 includes a PCB assembly 906. PCB assembly 906 in turn includes battery contacts 907 for contacting battery 908, a thermistor 909, antennae 910 and processor 911. The PCB assembly may include additional optional components as discussed herein, e.g., as discussed in the context of data processing unit 102 above.

Sensor control unit insertion assembly 900 also includes sensor support 912 which is configured to hold insertion needle 902 and analyte sensor 913 together during the insertion process. Sensor support 912 may be made from a variety of suitable materials including, e.g., a suitable thermoplastic polymer material (e.g., Acetal). Analyte sensor 913 is depicted in this embodiment as a double-sided analyte sensor, e.g., a double-sided analyte sensor formed as depicted in analyte sensor assembly 500, as discussed previously herein. However, it should be noted that sensor control unit insertion assembly 900 may be readily modified to accept an analyte sensor having a different configuration discussed herein, e.g., a single-sided analyte sensor as discussed herein.

Sensor control unit insertion assembly 900 also includes a sensor connector, e.g., a rivet 914, which may be a rivet 600 as discussed previously herein. Where the analyte sensor 913 is, e.g., a double-sided analyte sensor formed as depicted in analyte sensor assembly 500, the rivet functions to physically and electrically connect analyte sensor 913 to PCB assembly 906. The rivet physically connects analyte sensor 913 to PCB assembly 906 such that electrical contacts 504A and 502B of the reference and working electrodes respectively (See FIG. 7) come into physical and electrical contact with electrical contacts on the top surface of PCB assembly 906. The rivet 914, made of a conductive material in this embodiment, also provides an electrical connection between electrical contact 507A of counter electrode 507 (See FIG. 7) and a electrical contact positioned on the bottom surface of PCB assembly 906 without providing a physical connection between electrical contact 507A and the electrical contact positioned on the bottom surface of PCB assembly 906 (in other words without bringing electrical contact 507A into physical contact with the electrical contact positioned on the bottom surface of PCB assembly 906).

In the embodiment shown in FIG. 22 overmold structure 905 is formed over PCB assembly 906 following attachment of sensor support 912, analyte sensor 913, and rivet 914 to PCB assembly 906. Following formation of the overmold structure 905, skin patch 904 is attached to form the sensor control unit insertion assembly 900.

FIG. 22 shows analyte sensor 913 in a bent configuration such that the distal end of the analyte sensor, which includes the analyte sensing region, is positioned at approximately a 90° angle relative to the plane of the PCB assembly 906. This configuration allows the distal end of the analyte sensor 913 to slideably engage needle 902 of the sensor insertion device 901 while the proximal end of the analyte sensor 913 including the electrode contacts is positioned in a facing relationship relative to the plane of PCB assembly 906.

Figure 21B:
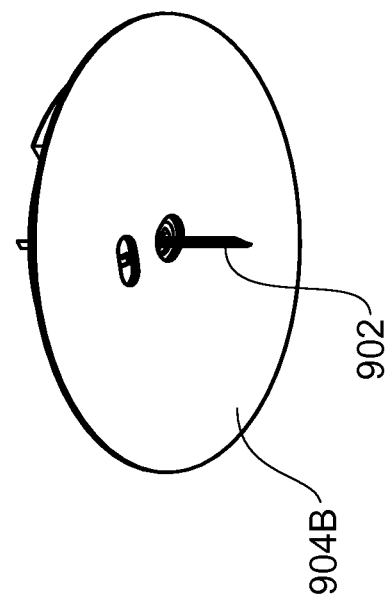
FIGS. 21A and 21B show a top perspective view and a bottom perspective view respectively of a sensor control unit insertion assembly according to one embodiment of the present disclosure.
Figure 21A:
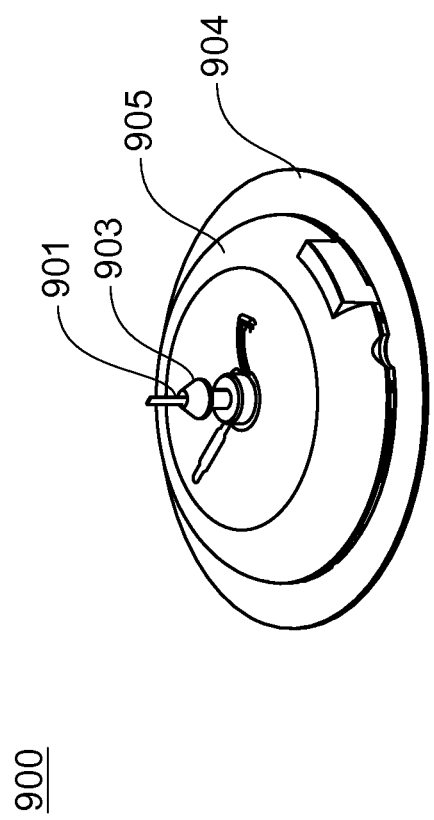
Figure 22:
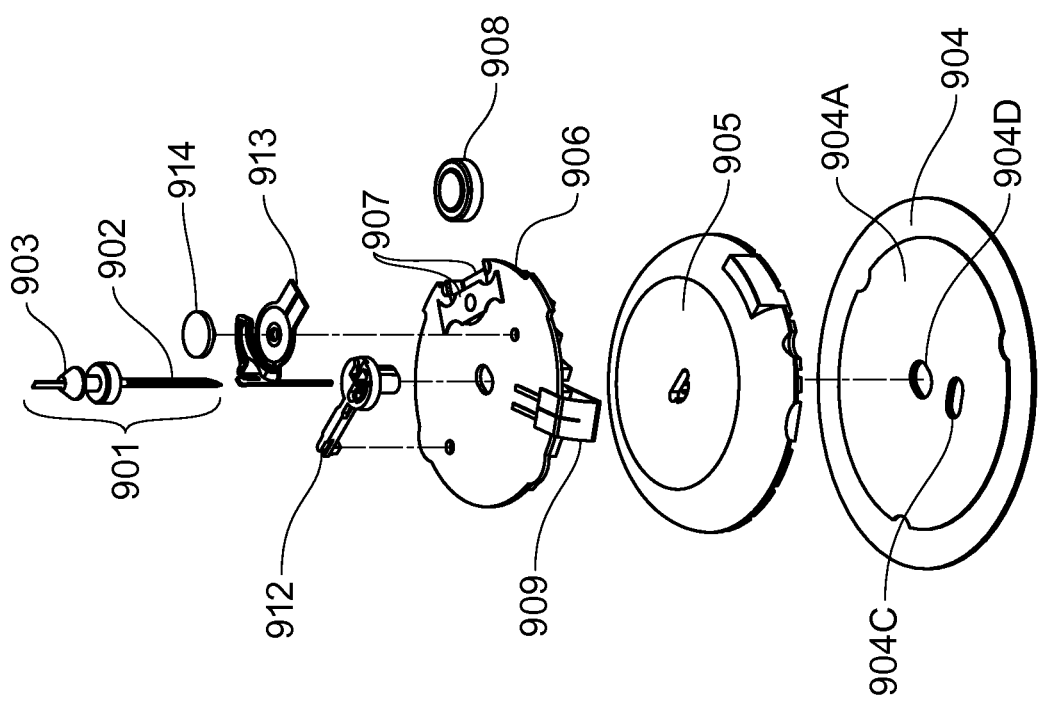
FIG. 22 provides a view which visually identifies the various components of the sensor control unit insertion assembly depicted in FIGS. 21A and 21B.
Figure 25C:
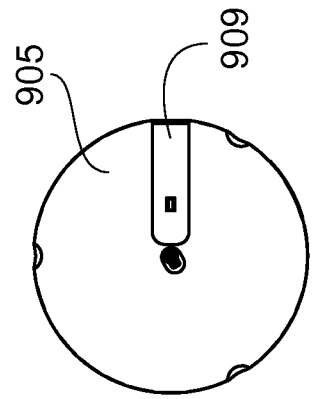
FIGS. 25A-25E provide a top view (25A), a side view (25B), a bottom view (25C), a top perspective view (25D) and a bottom perspective view (25E) of a portion of the sensor control unit insertion assembly depicted in FIGS. 21A and 21B including the PCB assembly, sensor support, analyte sensor, rivet, sensor insertion device and overmold structure. The optional thermistor of the PCB assembly is shown in completely folded configuration.
Figure 25B:
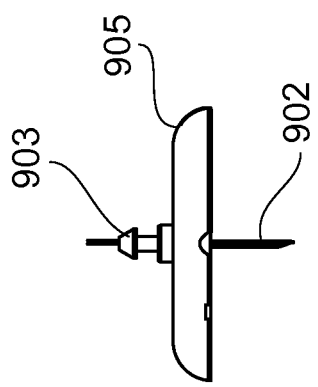
Figure 25A:
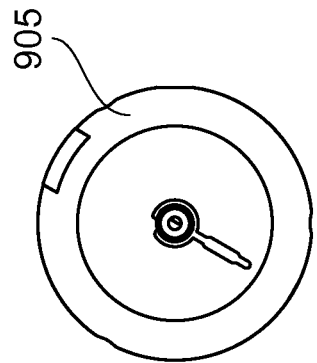
Figure 25E:
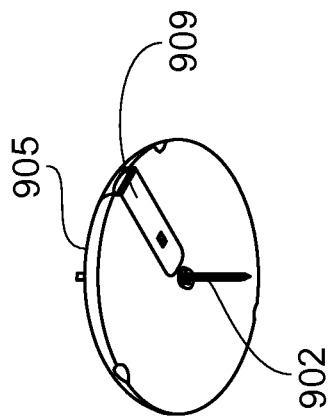
Figure 25D:
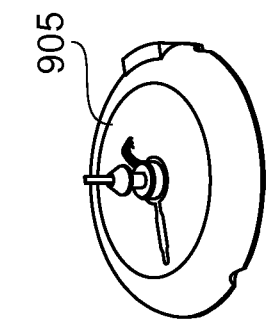
Figure 27:
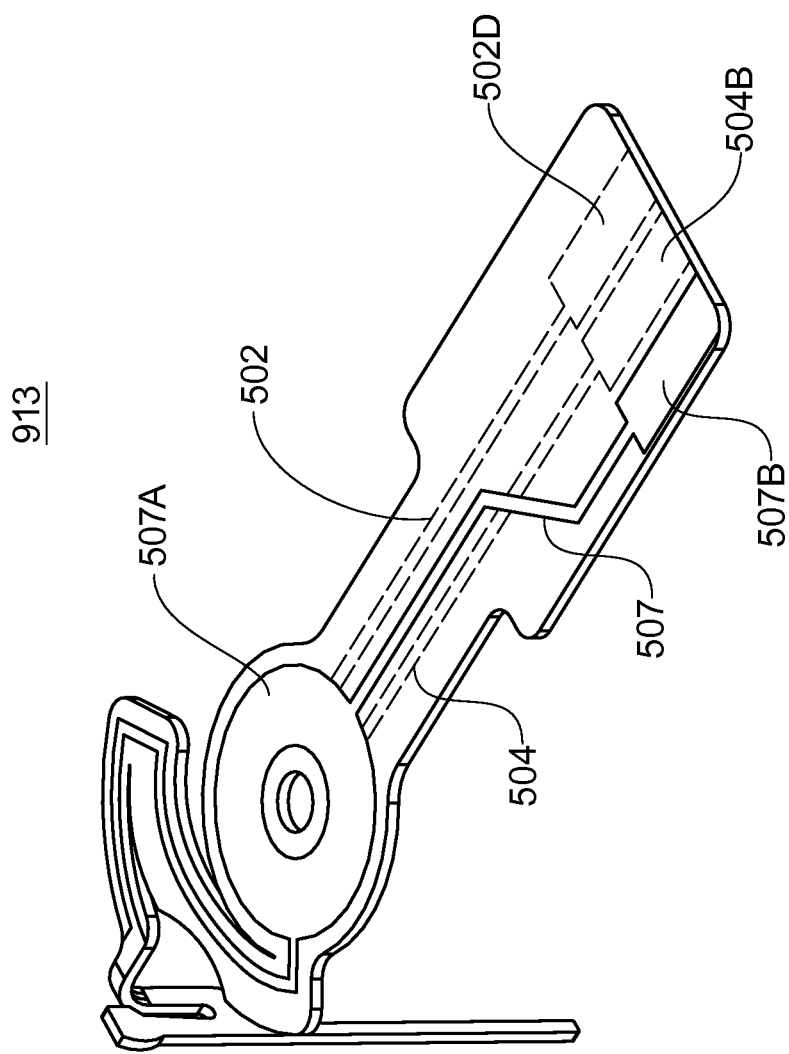
FIG. 27 provides a perspective view of an analyte sensor according to one embodiment of the present disclosure, wherein the analyte sensor is shown in a bent configuration suitable for insertion in connection with a sensor control unit insertion assembly as described herein. The analyte sensor is shown prior to cutting, e.g., along the cut line shown in FIG. 7.

FIGS. 23A-23G provides various views of a portion of the sensor control unit insertion assembly 900 depicted in FIGS. 21A and 21B including PCB assembly 906, sensor support 912, analyte sensor 913, rivet 914 and sensor insertion device 901. The analyte sensor 913 is shown prior to cutting, e.g., along the cut line shown in FIG. 7, to remove excess sensor material. A larger view of this analyte sensor configuration is shown in FIG. 27. FIGS. 23A-23G also show various components of PCB assembly 906 including battery contacts 907 for contacting battery 908, a thermistor 909, antennae 910 and processor 911. Thermistor 909 is shown in a parallel configuration relative to the plane of the PCB assembly 906. Following formation of overmold structure 905, but prior to attachment of skin patch 904, thermistor 909 is folded under the base of the overmold structure 905 as shown in FIGS. 19A-25E. Skin patch 904 is then attached to the overmold structure leaving a portion of thermistor 909 exposed to the skin surface.

Sensor Control Unit Electronics

A sensor electronics unit, such as a sensor control unit, typically includes at least a portion of the electronic components that operate the sensor and the analyte detection/monitoring device and/or system. The electronic components of the sensor electronics unit typically include a power supply for operating the sensor control unit and the sensor, a sensor circuit for obtaining signals from and operating the sensor, a measurement circuit that converts sensor signals to a desired format, and a processing circuit that, at minimum, obtains signals from the sensor circuit and/or measurement circuit and provides the signals to an optional transmitter. In some embodiments, the processing circuit may also partially or completely evaluate the signals from the sensor and convey the resulting data to an optional transmitter and/or activate an optional alarm system if the analyte level exceeds a threshold. The processing circuit often includes digital logic circuitry.

The sensor electronics unit may optionally contain a transmitter for transmitting the sensor signals or processed data from the processing circuit to a receiver/display unit; a data storage unit for temporarily or permanently storing data from the processing circuit; a temperature probe circuit for receiving signals from and operating a temperature probe; a reference voltage generator for providing a reference voltage for comparison with sensor-generated signals; and/or a watchdog circuit that monitors the operation of the electronic components in the sensor electronics unit. In some embodiments, the sensor electronics unit includes an RFID sensor or reader.

Moreover, the sensor electronics unit may also include digital and/or analog components utilizing semiconductor devices, including transistors. To operate these semiconductor devices, the sensor control unit may include other components including, for example, a bias control generator to correctly bias analog and digital semiconductor devices, an oscillator to provide a clock signal, and a digital logic and timing component to provide timing signals and logic operations for the digital components of the circuit.

As an example of the operation of these components, the sensor circuit and the optional temperature probe circuit provide raw signals from the sensor to the measurement circuit. The measurement circuit converts the raw signals to a desired format, using for example, a current-to-voltage converter, current-to-frequency converter, and/or a binary counter or other indicator that produces a signal proportional to the absolute value of the raw signal. This may be used, for example, to convert the raw signal to a format that can be used by digital logic circuits. The processing circuit may then, optionally, evaluate the data and provide commands to operate the electronics.

Calibration

Sensors may be configured to require no system calibration or no user calibration. For example, a sensor may be factory calibrated and need not require further calibrating. In certain embodiments, calibration may be required, but may be done without user intervention, i.e., may be automatic. In those embodiments in which calibration by the user is required, the calibration may be according to a predetermined schedule or may be dynamic, i.e., the time for which may be determined by the system on a real-time basis according to various factors, including, but not limited to, glucose concentration and/or temperature and/or rate of change of glucose, etc.

In addition to a transmitter, an optional receiver may be included in the sensor control unit. In some cases, the transmitter is a transceiver, operating as both a transmitter and a receiver. The receiver may be used to receive calibration data for the sensor. The calibration data may be used by the processing circuit to correct signals from the sensor. This calibration data may be transmitted by the receiver/display unit or from some other source such as a control unit in a doctor's office. In addition, the optional receiver may be used to receive a signal from the receiver/display units to direct the transmitter, for example, to change frequencies or frequency bands, to activate or deactivate the optional alarm system and/or to direct the transmitter to transmit at a higher rate.

Calibration data may be obtained in a variety of ways. For instance, the calibration data may be factory-determined calibration measurements which can be input into the sensor control unit using the receiver or may alternatively be stored in a calibration data storage unit within the sensor control unit itself (in which case a receiver may not be needed). The calibration data storage unit may be, for example, a readable or readable/writeable memory circuit. In some cases, a system may only need to be calibrated once during the manufacturing process, where recalibration of the system is not required.

If necessary, calibration may be accomplished using an in vitro test strip (or other reference), e.g., a small sample test strip such as a test strip that requires less than about 1 microliter of sample (for example Freestyle® or Precision™ blood glucose monitoring test strips from Abbott Diabetes Care, Alameda, Calif.). For example, test strips that require less than about 1 nanoliter of sample may be used. In certain embodiments, a sensor may be calibrated using only one sample of body fluid per calibration event. For example, a user need only lance a body part one time to obtain a sample for a calibration event (e.g., for a test strip), or may lance more than one time within a short period of time if an insufficient volume of sample is firstly obtained. Embodiments include obtaining and using multiple samples of body fluid for a given calibration event, where glucose values of each sample are substantially similar. Data obtained from a given calibration event may be used independently to calibrate or combined with data obtained from previous calibration events, e.g., averaged including weighted averaged, etc., to calibrate. In certain embodiments, a system need only be calibrated once by a user, where recalibration of the system is not required.

Alternative or additional calibration data may be provided based on tests performed by a health care professional or by the user. For example, it is common for diabetic individuals to determine their own blood glucose concentration using commercially available testing kits. The results of this test is input into the sensor control unit either directly, if an appropriate input device (e.g., a keypad, an optical signal receiver, or a port for connection to a keypad or computer) is incorporated in the sensor control unit, or indirectly by inputting the calibration data into the receiver/display unit and transmitting the calibration data to the sensor control unit.

Other methods of independently determining analyte levels may also be used to obtain calibration data. This type of calibration data may supplant or supplement factory-determined calibration values.

In some embodiments of the invention, calibration data may be required at periodic intervals, for example, every eight hours, once a day, or once a week, to confirm that accurate analyte levels are being reported. Calibration may also be required each time a new sensor is implanted or if the sensor exceeds a threshold minimum or maximum value or if the rate of change in the sensor signal exceeds a threshold value. In some cases, it may be necessary to wait a period of time after the implantation of the sensor before calibrating to allow the sensor to achieve equilibrium. In some embodiments, the sensor is calibrated only after it has been inserted. In other embodiments, no calibration of the sensor is needed.

Analyte Monitoring Device

In some embodiments of the invention, an analyte monitoring device is provided which includes a sensor electronics unit, such as a sensor control unit, and a sensor. In these embodiments, the processing circuit of the sensor electronics unit may be configured to determine a level of the analyte and activate an alarm system if the analyte level exceeds a threshold value. The sensor electronics unit, in these embodiments, may include an alarm system and may also include a display, such as an LCD or LED display.

A threshold value is exceeded if the datapoint has a value that is beyond the threshold value in a direction indicating a particular condition. For example, a datapoint which correlates to a glucose level of 200 mg/dL exceeds a threshold value for hyperglycemia of 180 mg/dL, because the datapoint indicates that the user has entered a hyperglycemic state. As another example, a datapoint which correlates to a glucose level of 65 mg/dL exceeds a threshold value for hypoglycemia of 70 mg/dL because the datapoint indicates that the user is hypoglycemic as defined by the threshold value. However, a datapoint which correlates to a glucose level of 75 mg/dL would not exceed the same threshold value of 70 mg/dL for hypoglycemia because the datapoint does not indicate that particular condition as defined by the chosen threshold value.

An alarm may also be activated if the sensor readings indicate a value that is outside of (e.g., above or below) a measurement range of the sensor. For glucose, the physiologically relevant measurement range is typically 40-500 mg/dL, including 40-300 mg/dL and 50-250 mg/dL, of glucose in the interstitial fluid, and 20-500 mg/dL in blood.

The alarm system may also, or alternatively, be activated when the rate of change or acceleration of the rate of change in analyte level increase or decrease reaches or exceeds a threshold rate or acceleration. For example, in the case of a subcutaneous glucose monitor, the alarm system may be activated if the rate of change in glucose concentration exceeds a threshold value which may indicate that a hyperglycemic or hypoglycemic condition is likely to occur. In some cases, the alarm system is activated if the acceleration of the rate of change in glucose concentration exceeds a threshold value which may indicate that a hyperglycemic or hypoglycemic condition is likely to occur.

A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

Drug Delivery System

The subject invention also includes sensors and associated devices used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a processing unit such as a transmitter, a receiver/display unit, and a drug administration system. In some cases, some or all components may be integrated in a single unit. A sensor-based drug delivery system may use data from the one or more sensors to provide necessary input for a control algorithm/mechanism to adjust the administration of drugs, e.g., automatically or semi-automatically. As an example, a glucose sensor may be used to control and adjust the administration of insulin from an external or implanted insulin pump.

Fiducial Mark

A fiducial mark may be provided in connection with the manufacture of an analyte sensor, e.g., on a substrate layer of the analyte sensor. The fiducial mark provides a means by which the location of the electrode, e.g., the electrode trace, may be identified and/or located during the manufacturing process, e.g., to facilitate a singulation step.

Insertion Device

An insertion device can be used to subcutaneously insert the sensor into the user. The insertion device is typically formed using structurally rigid materials, such as metal or rigid plastic. Materials may include stainless steel and ABS (acrylonitrile-butadiene-styrene) plastic. In some embodiments, the insertion device is pointed and/or sharp at the tip to facilitate penetration of the skin of the user. A sharp, thin insertion device may reduce pain felt by the user upon insertion of the sensor. In other embodiments, the tip of the insertion device has other shapes, including a blunt or flat shape. These embodiments may be useful when the insertion device does not penetrate the skin but rather serves as a structural support for the sensor as the sensor is pushed into the skin.

In one embodiment, a sensor insertion device 901 is provided as a component of a sensor control unit insertion assembly 900. See, e.g., FIGS. 21A-26E. Sensor insertion device 901 includes an insertion needle 902, e.g., a slotted needle, and a needle hub assembly 903.

Examples of sensor insertion devices and methods of using the same are disclosed in U.S. application Ser. Nos. 13/071,461; 13/071,487; and 13/071,497, which were all filed on Mar. 24, 2011 and are all titled "Medical Device Inserters And Processes of Inserting And Using Medical Devices," the disclosures of each of which are incorporated herein by reference in their entirety.

EMBODIMENTS

In some embodiments, an analyte monitoring device is provided, which includes: an analyte sensor including a first conductive trace, and a dielectric substrate layer having a top surface and a bottom surface, wherein the first conductive trace is positioned on the top surface of the dielectric substrate layer; a printed circuit board (PCB) including a top surface and a bottom surface; and a rivet, wherein the analyte sensor is attached to the PCB by the rivet.

In some embodiments of the analyte monitoring device, the rivet includes a conductive material and provides an electrical connection between the first conductive trace and the PCB through the dielectric substrate layer. In one such embodiment, the conductive material is copper.

In some embodiments of the analyte monitoring device, the analyte sensor includes a second conductive trace positioned on the bottom surface of the dielectric substrate layer.

In some embodiments of the analyte monitoring device, where the rivet includes a conductive material and provides an electrical connection between the first conductive trace and the PCB through the dielectric substrate layer, the analyte sensor includes a second conductive trace positioned on the bottom surface of the dielectric substrate layer. In one such embodiment the conductive material is copper.

In other embodiments, an analyte monitoring device is provided, which includes: an analyte sensor including first, second, third and fourth dielectric layers, each layer having a top surface and a bottom surface, a first conductive trace positioned between the top surface of the first dielectric layer and the bottom surface of the second dielectric layer, a second conductive trace positioned between the bottom surface of the first dielectric layer and the top surface of the third dielectric layer, a third conductive trace positioned between the bottom surface of the third dielectric layer and the top surface of the fourth dielectric layer; a printed circuit board (PCB) including a top surface and a bottom surface; and a rivet, wherein the analyte sensor is attached to the PCB by the rivet.

In some embodiments of the analyte monitoring device, the rivet includes a conductive material and provides an electrical connection between the first conductive trace and the PCB through one or more of the dielectric layers.

In some embodiments of the analyte monitoring device, where the rivet includes a conductive material and provides an electrical connection between the first conductive trace and the PCB through one or more of the dielectric layers, the rivet provides an electrical connection between the first conductive trace and the bottom surface of the PCB. In one such embodiment, the second electrode trace and the third electrode trace each include an electrical contact configured to contact the top surface of the PCB.

In some embodiments of the analyte monitoring device, where the rivet includes a conductive material and provides an electrical connection between the first conductive trace and the PCB through one or more of the dielectric layers, the conductive material is copper.

In some embodiments of the analyte monitoring device, where the rivet includes a conductive material and provides an electrical connection between the first conductive trace and the PCB through one or more of the dielectric layers, the first conductive trace is a counter electrode trace, the second conductive trace is a working electrode trace, and the third conductive trace is a reference electrode trace. In one such embodiment, the working electrode trace and the reference electrode trace each include a electrical contact configured to contact the top surface of the PCB.

In some embodiments, a method of making an analyte monitoring device is provided, which includes: providing an analyte sensor including a first conductive trace, and a dielectric substrate layer having a top surface and a bottom surface, wherein the first conductive trace is positioned on the top surface of the dielectric substrate layer, and wherein the dielectric layer includes a through-hole; providing a printed circuit board (PCB) including a through-hole, a top surface and a bottom surface; and attaching the analyte sensor to the PCB by forming a rivet which extends through the respective through-holes of the dielectric substrate layer and the PCB.

In some embodiments of the method of making the analyte monitoring device, the rivet includes a conductive material and provides an electrical connection between the first conductive trace and the PCB through the dielectric substrate layer. In one such embodiment, the conductive material is copper.

In some embodiments of the method of making the analyte monitoring device, the analyte sensor includes a second conductive trace positioned on the bottom surface of the dielectric substrate layer.

In some embodiments of the method of making the analyte monitoring device, where the rivet includes a conductive material and provides an electrical connection between the first conductive trace and the PCB through the dielectric substrate layer, the analyte sensor includes a second conductive trace positioned on the bottom surface of the dielectric substrate layer. In one such embodiment, the conductive material is copper.

In some embodiments, a method of making an analyte monitoring device is provided, which includes: providing an analyte sensor including first, second, third and fourth dielectric layers, each dielectric layer having a top surface and a bottom surface, a first conductive trace positioned between the top surface of the first dielectric layer and the bottom surface of the second dielectric layer, wherein the first dielectric layer includes a through-hole, a second conductive trace positioned between the bottom surface of the first dielectric layer and the top surface of the third dielectric layer, a third conductive trace positioned between the bottom surface of the third dielectric layer and the top surface of the fourth dielectric layer; providing a printed circuit board (PCB) including a through-hole, a top surface and a bottom surface; and attaching the analyte sensor to the PCB by forming a rivet which extends through the respective through-holes of the first dielectric layer and the PCB.

In some embodiments of the method of making the analyte monitoring device, the rivet includes a conductive material and provides an electrical connection between the first conductive trace and the PCB through one or more of the dielectric layers.

In some embodiments of the method of making the analyte monitoring device, where the rivet includes a conductive material and provides an electrical connection between the first conductive trace and the PCB through one or more of the dielectric layers, the rivet provides an electrical connection between the first conductive trace and the bottom surface of the PCB. In one such embodiment, the second electrode trace and the third electrode trace each include an electrical contact configured to contact the top surface of the PCB.

In some embodiments of the method of making the analyte monitoring device, where the rivet includes a conductive material and provides an electrical connection between the first conductive trace and the PCB through one or more of the dielectric layers, the conductive material is copper.

In some embodiments of the method of making the analyte monitoring device, where the rivet includes a conductive material and provides an electrical connection between the first conductive trace and the PCB through one or more of the dielectric layers, the first conductive trace is a counter electrode trace, the second conductive trace is a working electrode trace, and the third conductive trace is a reference electrode trace. In one such embodiment, the working electrode trace and the reference electrode trace each include an electrical contact configured to contact the top surface of the PCB.

In some embodiments, an analyte sensor is provided, which includes: a dielectric base substrate having a proximal end, a distal end, a first side edge extending from the proximal end to the distal end, a second side edge extending from the proximal end to the distal end, and a first thickness; a first conductive layer positioned on the dielectric base substrate, the first conductive layer having a length ($L_1$) and a width ($W_1$); a first dielectric cover layer positioned to cover at least a portion of the first conductive layer, wherein the first dielectric cover layer has a proximal end, a distal end, a first side edge extending from the proximal end to the distal end, a second side edge extending from the proximal end to the distal end, and a second thickness which is less than that of the dielectric base substrate; a second conductive layer positioned on the first dielectric cover layer, the second conductive layer having a length ($L_2$) and a width ($W_2$); and a second dielectric cover layer positioned to cover at least a portion of the second conductive layer, wherein the second dielectric cover layer has a second thickness which is less than that of the dielectric base substrate, wherein $W_1$ is less than $W_2$ or $W_2$ is less than $W_1$.

In some embodiments of the analyte sensor, when $W_1$ is less than $W_2$ the first conductive layer is spaced away from the first and second side edges of the dielectric base substrate. In one such embodiment, the second conductive layer terminates at a distal end which is spaced back from the distal end of the first conductive layer.

In some embodiments of the analyte sensor, when $W_2$ is less than $W_1$ the second conductive layer is spaced away from the first and second side edges of the first dielectric cover layer. In one such embodiment, the second conductive layer terminates at a distal end which is spaced back from the distal end of the first conductive layer.

In some embodiments, an analyte monitoring device is provided which includes: an analyte sensor including a first electrode, and a dielectric substrate layer having a first surface and a second surface, wherein the first electrode is positioned on the first surface of the dielectric substrate layer; a printed circuit board (PCB) comprising a first surface and a second surface; and a rivet, wherein the analyte sensor is attached to the PCB by the rivet.

In some embodiments of the analyte monitoring device, the rivet includes a conductive material and provides an electrical connection between the first electrode and the PCB through the dielectric substrate layer. In some embodiments, the conductive material is copper.

In some embodiments of the analyte monitoring device, the analyte sensor includes a second electrode positioned on the second surface of the dielectric substrate layer.

In some embodiments of the analyte monitoring device the first electrode comprises carbon or gold.

In some embodiments, an analyte monitoring device includes: an analyte sensor including first, second, third and fourth dielectric layers, each layer having a first surface and a second surface, a first electrode positioned between the first surface of the first dielectric layer and the second surface of the second dielectric layer, a second electrode positioned between the second surface of the first dielectric layer and the first surface of the third dielectric layer, a third electrode positioned between the second surface of the third dielectric layer and the first surface of the fourth dielectric layer; a printed circuit board (PCB) comprising a first surface and a second surface; and a rivet, wherein the analyte sensor is attached to the PCB by the rivet.

In some embodiments of the analyte monitoring device, the rivet includes a conductive material and provides an electrical connection between the first electrode and the PCB through one or more of the dielectric layers.

In some embodiments of the analyte monitoring device, the rivet provides an electrical connection between the first electrode and the second surface of the PCB.

In some embodiments of the analyte monitoring device, the second electrode and the third electrode each include an electrical contact configured to contact the first surface of the PCB.

In some embodiments of the analyte monitoring device, the first electrode is a counter electrode, the second electrode is a working electrode, and the third electrode is a reference electrode.

In some embodiments of the analyte monitoring device, the working electrode and the reference electrode each include an electrical contact configured to contact the first surface of the PCB.

In some embodiments of the analyte monitoring device the first, second, and third electrodes comprise carbon or gold.

In some embodiments, a method of making an analyte monitoring device includes: providing an analyte sensor including a first electrode, and a dielectric substrate layer having a first surface and a second surface, wherein the first electrode is positioned on the first surface of the dielectric substrate layer, and wherein the dielectric layer includes a through-hole; providing a printed circuit board (PCB) comprising a through-hole, a first surface and a second surface; and attaching the analyte sensor to the PCB by forming a rivet which extends through the respective through-holes of the dielectric substrate layer and the PCB.

In some embodiments of the method of making the analyte monitoring device, the rivet includes a conductive material and provides an electrical connection between the first electrode and the PCB through the dielectric substrate layer.

In some embodiments of the method of making the analyte monitoring device, the conductive material is copper.

In some embodiments of the method of making the analyte monitoring device, the analyte sensor includes a second electrode positioned on the second surface of the dielectric substrate layer.

In some embodiments of the method of making the analyte monitoring device, the first electrode comprises carbon or gold.

In some embodiments, a method of making an analyte monitoring device includes: providing an analyte sensor including first, second, third and fourth dielectric layers, each dielectric layer having a first surface and a second surface, a first electrode positioned between the first surface of the first dielectric layer and the second surface of the second dielectric layer, wherein the first dielectric layer includes a through-hole, a second electrode positioned between the second surface of the first dielectric layer and the first surface of the third dielectric layer, a third electrode positioned between the second surface of the third dielectric layer and the first surface of the fourth dielectric layer; providing a printed circuit board (PCB) comprising a through-hole, a first surface and a second surface; and attaching the analyte sensor to the PCB by forming a rivet which extends through the respective through-holes of the first dielectric layer and the PCB.

In some embodiments of the method of making an analyte monitoring device, the rivet includes a conductive material and provides an electrical connection between the first electrode and the PCB through one or more of the dielectric layers.

In some embodiments of the method of making an analyte monitoring device, the rivet provides an electrical connection between the first electrode and the second surface of the PCB.

In some embodiments of the method of making an analyte monitoring device, the second electrode and the third electrode each include an electrical contact configured to contact the first surface of the PCB.

In some embodiments of the method of making an analyte monitoring device, the conductive material is copper.

In some embodiments of the method of making an analyte monitoring device, the first electrode is a counter electrode, the second electrode is a working electrode, and the third electrode is a reference electrode.

In some embodiments of the method of making an analyte monitoring device, the working electrode and the reference electrode each include an electrical contact configured to contact the first surface of the PCB.

In some embodiments of the method of making an analyte monitoring device, the first, second, and third electrodes comprise carbon or gold.

In some embodiments, an analyte sensor includes: a dielectric base substrate having a proximal end, a distal end, a first side edge extending from the proximal end to the distal end, a second side edge extending from the proximal end to the distal end, and a first thickness; a first conductive layer positioned on the dielectric base substrate, the first conductive layer having a length (L1) and a width (W1); a first dielectric cover layer positioned to cover at least a portion of the first conductive layer, wherein the first dielectric cover layer has a proximal end, a distal end, a first side edge extending from the proximal end to the distal end, a second side edge extending from the proximal end to the distal end, and a second thickness which is less than that of the dielectric base substrate; a second conductive layer positioned on the first dielectric cover layer, the second conductive layer having a length (L2) and a width (W2); and a second dielectric cover layer positioned to cover at least a portion of the second conductive layer, wherein the second dielectric cover layer has a second thickness which is less than that of the dielectric base substrate, wherein W1 is less than W2 or W2 is less than W1.

In some embodiments of the analyte sensor, when W1 is less than W2 the first conductive layer is spaced away from the first and second side edges of the dielectric base substrate.

In some embodiments of the analyte sensor, the second conductive layer terminates at a distal end which is spaced back from the distal end of the first conductive layer.

In some embodiments of the analyte sensor, when W2 is less than W1 the second conductive layer is spaced away from the first and second side edges of the first dielectric cover layer.

In some embodiments of the analyte sensor, the second conductive layer terminates at a distal end which is spaced back from the distal end of the first conductive layer.

In some embodiments of the analyte sensor, the first and second conductive layers comprise carbon or gold.

In some embodiments, a system includes: a sensor connector; an analyte sensor; and an electronics unit, wherein the sensor connector is configured to physically, electrically, or physically and electrically connect the analyte sensor and the electronics unit.

In some embodiments of the system, the sensor connector is a rivet comprising a first end and a second end.

In some embodiments of the system, the rivet includes a conductive material.

In some embodiments of the system, the rivet physically and electrically connects the analyte sensor and the electronics unit.

In some embodiments of the system, the rivet includes a rivet head positioned at the first end and a shaft extending from the rivet head to the second end, and wherein an angle formed by the rivet head and the shaft is less than 90 degrees.

In some embodiments of the system, the rivet includes a rivet head positioned at the first end and a shaft extending from the rivet head to the second end, and wherein the shaft includes a hole at the second end, the hole extending from the second end towards the first end terminating between the first end and the second end.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. This is intended to provide support for all such combinations.

Each of the various references, presentations, publications, provisional and/or non-provisional U.S. patent applications, U.S. patents, non-U.S. patent applications, and/or non-U.S. patents that have been identified herein, is incorporated herein by reference in its entirety and for all purposes.

Other embodiments and modifications within the scope of the present disclosure will be apparent to those skilled in the relevant art. Various modifications, processes, as well as numerous structures to which the embodiments of the invention may be applicable will be readily apparent to those of skill in the art to which the invention is directed upon review of the specification. Various aspects and features of the invention may have been explained or described in relation to understandings, beliefs, theories, underlying assumptions, and/or working or prophetic examples, although it will be understood that the invention is not bound to any particular understanding, belief, theory, underlying assumption, and/or working or prophetic example. Although various aspects and features of the invention may have been described largely with respect to applications, or more specifically, medical applications, involving diabetic humans, it will be understood that such aspects and features also relate to any of a variety of applications involving non-diabetic humans and any and all other animals. Further, although various aspects and features of the invention may have been described largely with respect to applications involving partially implanted sensors, such as transcutaneous or subcutaneous sensors, it will be understood that such aspects and features also relate to any of a variety of sensors that are suitable for use in connection with the body of an animal or a human, such as those suitable for use as fully implanted in the body of an animal or a human. Finally, although the various aspects and features of the invention have been described with respect to various embodiments and specific examples herein, all of which may be made or carried out conventionally, it will be understood that the invention is entitled to protection within the full scope of the appended claims.

That which is claimed is:

1. An electrode arrangement, comprising:
   a base substrate;
   a first conductive layer having a width ($W_1$) and positioned on the base substrate;
   a first dielectric layer positioned over at least a portion of the first conductive layer; and
   a second conductive layer having a with ($W_2$) and positioned on the first dielectric layer, wherein $W_1$ is less than $W_2$ or $W_2$ is less than $W_1$.

2. The electrode arrangement of claim 1, wherein when $W_1$ is less than $W_2$ the first conductive layer is spaced away from the first and second side edges of the dielectric base substrate.

3. The electrode arrangement of claim 2, wherein the second conductive layer terminates at a distal end which is spaced back from the distal end of the first conductive layer.

4. The electrode arrangement of claim 1, wherein when $W_2$ is less than $W_1$ the second conductive layer is spaced away from the first and second side edges of the first dielectric cover layer.

5. The electrode arrangement of claim 4, wherein the second conductive layer terminates at a distal end which is spaced back from the distal end of the first conductive layer.

6. The electrode arrangement of claim 1, wherein the first and second conductive layers comprise carbon or gold.

7. The electrode arrangement of claim 1, wherein $W_1$ is less than $W_2$.

8. The electrode arrangement of claim 1, wherein $W_2$ is less than $W_1$.

9. The electrode arrangement of claim 1, wherein $W_1$ is less than the width of the dielectric base substrate, the width of the first dielectric cover layer and the width of the second dielectric cover layer.

10. The electrode arrangement of claim 1, wherein $W_2$ is less than the width of the dielectric base substrate, the width of the first dielectric cover layer and the width of the second dielectric cover layer.

11. The electrode arrangement of claim 1, further comprising a conductive strip positioned in contact with the second conductive layer and having a width that is the same as the width of the dielectric base substrate, the width of the first dielectric cover layer and the width of the second dielectric cover layer.

12. The electrode arrangement of claim 1, wherein the first conductive layer has a length ($L_1$) and the second conductive layer has a length ($L_2$).

13. The electrode arrangement of claim 11, wherein the conductive strip has a length that is less than $L_1$ and $L_2$.

14. The electrode arrangement of claim 11, wherein the conductive strip is positioned orthogonal to the second conductive layer.

15. The electrode arrangement of claim 11, wherein the conductive strip comprises a material that is different from the second conductive layer.

16. The electrode arrangement of claim 15, wherein the second conductive material comprises carbon and the conductive strip comprises Ag/AgCl.

17. The electrode arrangement of claim 1, wherein the first conductive layer comprises one or more sensing elements, the sensing elements comprising an analyte responsive enzyme and a mediator.

18. The electrode arrangement of claim 17, wherein the mediator comprises an osmium transition metal complex.

19. The electrode arrangement of claim 17, further comprising a mass transport limiting layer comprising crosslinked polymers containing heterocyclic nitrogen-containing groups.

20. The electrode arrangement of claim 19, wherein the mass transport limiting layer comprises one or more leveling agents.

21. The electrode arrangement of claim 20, wherein the leveling agent is polydimethylsiloxane.

22. The electrode arrangement of claim 1, wherein first dielectric cover has a thickness which is less than that of the base substrate.

23. The electrode arrangement of claim 22, further comprising a second dielectric layer positioned to cover at least a portion of the second conductive layer, wherein the second dielectric cover layer has a second thickness which is less than that of the dielectric base substrate.

\* \* \* \* \*